US009891221B2

(12) United States Patent
Tsionsky et al.

(10) Patent No.: US 9,891,221 B2
(45) Date of Patent: *Feb. 13, 2018

(54) KITS SUITABLE FOR USE IN ELECTROCHEMILUMINESCENCE METHODS AND METHODS OF EFFECTING A SPECIFIC-BINDING NON-WASH ASSAY

(71) Applicant: Meso Scale Technologies, LLC., Rockville, MD (US)

(72) Inventors: Michael Tsionsky, Derwood, MD (US); Eli N. Glezer, Del Mar, CA (US); Selen Stromgren, Rockville, MD (US); George Sigal, Rockville, MD (US); Jonathan K. Leland, Silver Spring, MD (US); Mark A. Billadeau, Knoxville, MD (US); Svetlana Leytner, Austin, TX (US); Mark Martin, Rockville, MD (US); Larry Helms, Germantown, MD (US)

(73) Assignee: Meso Scale Technologies, LLC., Rockville, MD (US)

( * ) Notice: Subject to any disclaimer, the term of this patent is extended or adjusted under 35 U.S.C. 154(b) by 531 days.

This patent is subject to a terminal disclaimer.

(21) Appl. No.: 14/319,167

(22) Filed: Jun. 30, 2014

(65) Prior Publication Data

US 2014/0336070 A1 Nov. 13, 2014

Related U.S. Application Data

(60) Continuation of application No. 12/368,742, filed on Feb. 10, 2009, now Pat. No. 8,785,201, which is a division of application No. 11/055,472, filed on Feb. 9, 2005, now Pat. No. 7,491,540, which is a division of application No. 10/238,437, filed on Sep. 10, 2002, now Pat. No. 6,919,173.

(60) Provisional application No. 60/318,289, filed on Sep. 10, 2001, provisional application No. 60/363,498, filed on Mar. 11, 2002.

(51) Int. Cl.

| | |
|---|---|
| ***C12Q 1/68*** | (2006.01) |
| ***G01N 31/00*** | (2006.01) |
| ***G01N 33/573*** | (2006.01) |
| ***C12Q 1/48*** | (2006.01) |
| ***G01N 33/543*** | (2006.01) |
| ***G01N 33/58*** | (2006.01) |
| ***G01N 21/76*** | (2006.01) |
| ***G01N 33/53*** | (2006.01) |

(52) U.S. Cl.

CPC ........... *G01N 33/573* (2013.01); *C12Q 1/485* (2013.01); *G01N 21/76* (2013.01); *G01N 33/5306* (2013.01); *G01N 33/54386* (2013.01); *G01N 33/58* (2013.01); *G01N 33/582* (2013.01); *G01N 2333/91205* (2013.01); *G01N 2458/30* (2013.01); *G01N 2458/40* (2013.01); *Y10S 435/967* (2013.01); *Y10S 435/968* (2013.01); *Y10T 436/10* (2015.01); *Y10T 436/108331* (2015.01)

(58) Field of Classification Search

None

See application file for complete search history.

(56) References Cited

U.S. PATENT DOCUMENTS

| | | | | |
|---|---|---|---|---|
| 5,300,439 | A | 4/1994 | Charlton | |
| 5,496,703 | A | 3/1996 | Babish et al. | |
| 5,599,681 | A | 2/1997 | Epstein et al. | |
| 5,667,981 | A | 9/1997 | Groffen et al. | |
| 5,763,198 | A | 6/1998 | Hirth et al. | |
| 5,846,485 | A * | 12/1998 | Leland | G01N 33/569 422/52 |
| 5,914,237 | A | 6/1999 | Godowski et al. | |
| 6,387,638 | B1 | 5/2002 | Ballinger et al. | |
| 6,689,772 | B1 | 2/2004 | Boschelli et al. | |
| 6,919,173 | B2 | 7/2005 | Tsionsky et al. | |
| 7,491,540 | B2 | 2/2009 | Tsionsky et al. | |
| 8,785,201 | B2 * | 7/2014 | Tsionsky | C12Q 1/485 436/18 |
| 2003/0207290 | A1 | 11/2003 | Kenten et al. | |
| 2009/0170121 | A1 | 7/2009 | Tsionsky et al. | |

FOREIGN PATENT DOCUMENTS

| | | |
|---|---|---|
| WO | WO 89/05977 | 6/1989 |
| WO | WO 98/35036 | 8/1998 |

OTHER PUBLICATIONS

Hudson et al., "Practical Immunology", Second Edition, Blackwell Scientific Publications, p. 336 (1980).

Communication under Rule 71(3) EPC dated Jun. 20, 2013 for Application No. 02 759 622.0-1408.

Knight A.W. et al., "Relationship Between Structural Attributes and Observed Electrogenerated Chemiluminescence (ECL) Activity of Tertiary Amines as Potential Analytes for the Tris(2,2-Bipyridine)Ruthenium(II) ECL Reaction", Analyst 121:101R-106R (1996).

Canadian Examination Report dated May 10, 2017 received in Canadian Patent Application No. 2,932,756.

* cited by examiner

*Primary Examiner* — Yunsoo Kim

(74) *Attorney, Agent, or Firm* — Scully, Scott, Murphy & Presser, P.C.

(57) ABSTRACT

The invention relates to improved electrochemiluminescence assay methods for phosphorylated peptides or proteins employing phospho-specific antibodies and buffer compositions that are substantially free of inorganic phosphate.

27 Claims, 6 Drawing Sheets

Assay Buffer Background
Signal
S/B
500
400
300
200
100
0
80,000
60,000
40,000
20,000
0
1,000
800
600
400
200
0
TPA /Phos
TPA/Tris
TPA/Gly-Gly
PIPES/Phos Assay Buffer Background
Signal
S/B
400
300
200
100
0
20,000
16,000
12,000
8,000
4,000
0
TPA - Phos
TPA - TRIS
TPA - GlyGly
PIPES - Phos Assay Buffer Background
100
0
None
Triton
Thesit
Tween
Signal
4,000
3,000
2,000
1,000
0
None
Triton
Thesit
Tween
S/B
50
40
30
20
10
0
None
Triton
Thesit
Tween Assay Buffer Background
400
300
200
100
0
None
Triton
Thesit
Tween
Signal
3,000
2,000
1,000
0
None
Triton
Thesit
Tween
S/B
10.0
8.0
6.0
4.0
2.0
0.0
None
Triton
Thesit
Tween

KITS SUITABLE FOR USE IN ELECTROCHEMILUMINESCENCE METHODS AND METHODS OF EFFECTING A SPECIFIC-BINDING NON-WASH ASSAY

CROSS-REFERENCE TO RELATED APPLICATIONS

This application is a continuation of copending application U.S. Ser. No. 12/368,742, filed Feb. 10, 2009, which is a divisional of application U.S. Ser. No. 11/055,472, filed Feb. 9, 2005, now U.S. Pat. No. 7,491,540, which is a divisional of application U.S. Ser. No. 10/238,437, filed Sep. 10, 2002, now U.S. Pat. No. 6,919,173, which claims priority to U.S. Provisional Application Ser. No. 60/318,289, filed Sep. 10, 2001, and U.S. Provisional Application Ser. No. 60/363,498, filed Mar. 11, 2002, each of which are hereby incorporated by reference.

1. FIELD OF THE INVENTION

This application relates to compositions for use in assays, particularly in electrochemiluminescent assays, and methods of using the same.

2. BACKGROUND OF THE INVENTION

At this time, there are a number of commercially available instruments that utilize electrochemiluminescence (ECL) for analytical measurements including drug screening. Species that can be induced to emit ECL (ECL-active species) have been used as ECL labels. Examples of ECL labels include: i) organometallic compounds where the metal is from, for example, the noble metals of group VIII, including Ru-containing and Os-containing organometallic compounds such as the tris-bipyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485, herein incorporated by reference), oxalate, and persulfate for ECL from RuBpy and hydrogen peroxide for ECL from luminol (see, e.g., U.S. Pat. No. 5,240,863). The light generated by ECL labels can be used as a reporter signal in diagnostic procedures (Bard et al., U.S. Pat. No. 5,238,808). For instance, an ECL label can be covalently coupled to a binding agent such as an antibody, nucleic acid probe, receptor or ligand; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants). For more background on ECL, ECL labels, ECL assays and instrumentation for conducting ECL assays see U.S. Pat. Nos. 5,093,268; 5,147,806; 5,324,457; 5,591,581; 5,597,910; 5,641,623; 5,643,713; 5,679,519; 5,705,402; 5,846,485; 5,866,434; 5,786,141; 5,731,147; 6,066,448; 6,136,268; 5,776,672; 5,308,754; 5,240,863; 6,207,369 and 5,589,136 and Published PCT Nos. WO99/63347; WO00/03233; WO99/58962; WO99/32662; WO99/14599; WO98/12539; WO97/36931 and WO98/57154.

Commercially available ECL instruments have demonstrated exceptional performance. They have become widely used for reasons including their excellent sensitivity, dynamic range, precision, and tolerance of complex sample matrices. The commercially available instrumentation uses flow cell-based designs with permanent reusable flow cells. Recently, ECL instrumentation has been disclosed that uses reagents immobilized on the electrode used to induce ECL (see, e.g., U.S. Pat. Nos. 6,140,045; 6,066,448; 6,090,545; 6,207,369 and Published PCT Application No. WO98/12539). Multi-well plates having integrated electrodes suitable for such ECL measurements have also been recently disclosed (see, e.g., U.S. application Ser. No. 10/185,274 (now U.S. Pat. No. 7,842,246) and Ser. No. 10/185,363 (now U.S. Pat. No. 6,977,722), each filed on Jun. 28, 2002 and hereby incorporated by reference). See also, U.S. application Ser. No. 10/238,391, filed on Sep. 10, 2002, now U.S. Pat. No. 7,858,321, which is hereby incorporated by reference.

Currently, pH buffers containing inorganic phosphate are employed in many electrochemiluminescence assays. Applicants have discovered that such pH buffers can, in certain assays, interfere with the assay and decrease the performance of the assay.

Accordingly, it would be desirable to find alternative pH assay buffers, compositions containing the same and methods of using the same for use in those assays which are detrimentally effected by pH buffers containing inorganic phosphate. It would also be desirable to find alternative ECL Assay Buffers with improved performance in ECL assays.

3. SUMMARY OF THE INVENTION

The present invention relates to improved compositions, reagents, kits, systems, system components, and methods for performing assays. More particularly, the invention relates to the use of novel combinations of reagents to provide improved assay performance.

One aspect of the invention relates to improved ECL Assay Buffers that comprise an ECL coreactant and, preferably, a pH buffering agent. The ECL Assay Buffers provide a suitable environment for efficiently inducing ECL labels to emit ECL and for sensitively measuring ECL labels via the measurement of ECL. The ECL Assay Buffers of the invention may optionally comprise additional components including detergents, preservatives, anti-foaming agents, ECL active species, salts, metal ions and/or metal chelating agents. The ECL Assay Buffers of the invention may also include components of a biological assay, which in some cases may be labeled with an ECL label, including binding reagents, enzymes, enzyme substrates, cofactors and/or enzyme inhibitors. The invention also includes assay reagents, compositions, kits, systems and system components that comprise the ECL Assay Buffers of the invention and, optionally, additional assay components. The invention also includes methods for conducting ECL assays using the ECL Assay Buffers of the invention.

Another aspect of the invention relates to the use of pH buffers which are substantially free of inorganic phosphates. Such buffers, in some applications, have been found to significantly improve the performance of ECL measurements. Such buffers have also been found to be advantageous in certain applications where phosphate has been found to interfere with a chemical, biochemical or biological reaction.

Surprisingly, such reagents provide a number of surprising advantages including improving the performance of assays employing phospho-specific antibodies (i.e., antibodies that specifically bind with a phospho-peptide, phospho-amino acid and/or phospho-protein). It is believed that these antibodies may have a low affinity for inorganic phosphate and that the elimination of the inorganic phosphate greatly reduces interference between the phosphate of the pH buffer and the phospho-specific antibodies. Accordingly, the invention includes method, reagents, kits and compositions for measuring phospho-peptides, phospho-amino acids or phospho-protein which use buffer compositions that are free or substantially free (e.g., below the levels that interfere with phospho-specific antibodies). Such methods, kits, compositions, and reagents are, preferably, applied to the measurement (most preferably using ECL detection) of protein kinase or phosphorylase activities through the specific measurement of reaction products or substrates.

Another aspect of the invention relates to compositions and reagents with that give high signal to background ratios in electrochemiluminescence assays. Such improved performance has been achieved through the identification of advantageous combinations of ECL coreactants, pH buffers, detergent and pH and, in particular, through the use of ECL coreactants and/or pH buffers other than TPA and phosphate. These improved formulations are of particular value in non-wash assays and high sensitivity assays. In some embodiments of the invention, the performance of ECL assays is improved even further through optimal combinations of reagent compositions with electrode compositions.

In some embodiments of the invention, the compositions and reagents of the invention improve the ratio of ECL signal from bound label to ECL signal from free label. This is particularly true in assays involving reagents immobilized on a solid surface such as an electrode. This is important, for example, in solid phase assays not having a wash step (especially in low affinity interaction assays) since the major component of the background signal comes from the labels present in solution.

yet another advantage of the invention relates to improved sensitivity of assays using the compositions of the invention. More specifically, the ECL Assay Buffers of the invention provide improved sensitivity at low detection levels by reducing the background electrochemiluminescence in the absence of ECL labels. Surprisingly, ECL Assay Buffers comprising pH buffering agents other than phosphate or which are substantially free of inorganic phosphate emit less background luminescence than conventional ECL Assay Buffers comprising inorganic phosphate based pH buffers. This is particularly advantages at low detection levels where increasing the signal to background ratio greatly improves the performance of the assay.

Another aspect of the invention relates to improved reagent kits comprising the ECL assay buffers, where the reagents include non-phosphate based pH buffering agents, the ECL assay buffers are substantially free of inorganic phosphate and/or the ECL assay buffers employ tertiary amine coreactants other than TPA. In particular, kits containing, in one or more containers, the ECL assay buffer and, preferably also containing one or more other assay components.

Another aspect of the invention relates to improved methods performed using the present invention, particularly assay methods employing phospho-specific antibodies, low detection limits, immobilized reagents and/or a non-wash formats.

Yet another aspect of the invention relates to improved systems and apparatus containing the compositions or reagents of the invention and/or improved systems and apparatus adapted to perform the improved methods of the invention.

4. DESCRIPTION OF THE FIGURES

FIG. 1 compares the rates of dissociation of a phosphopeptide-antiphosphopeptide complex in three different ECL Assay Buffers that comprise different pH buffering agents.

Figure 4A:
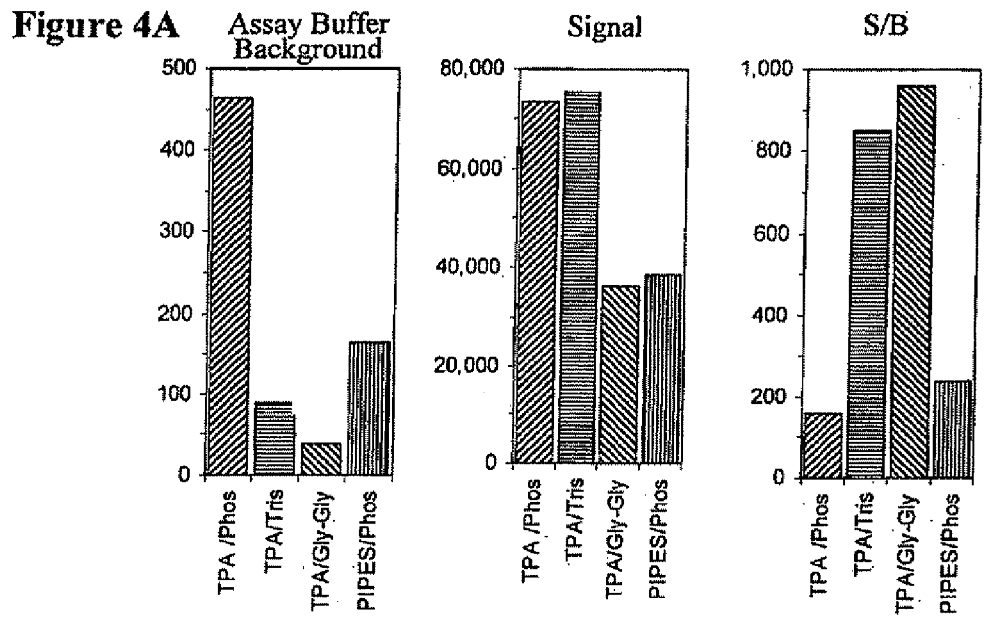
Figure 4B:
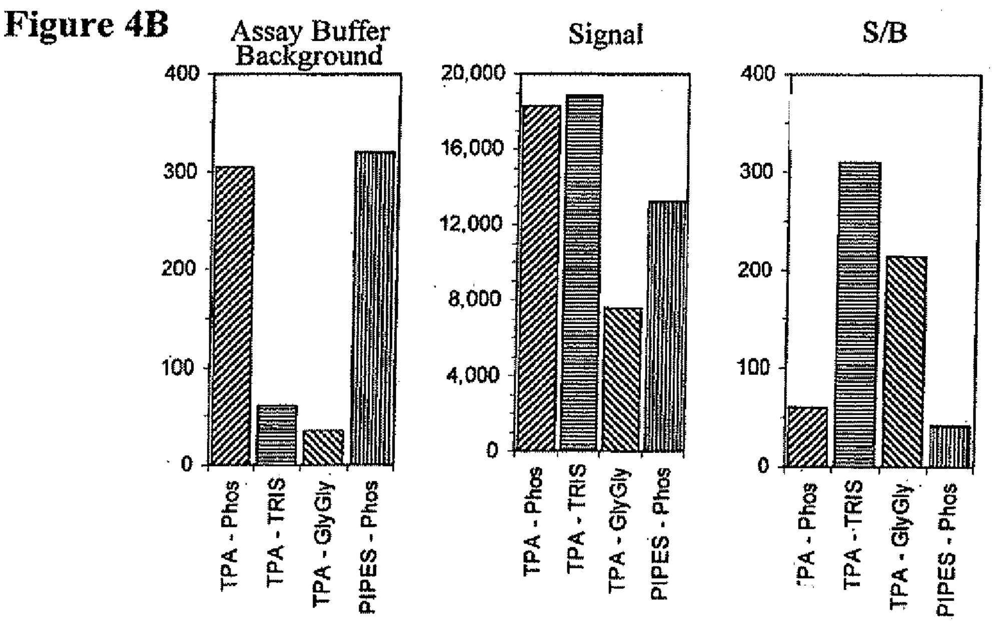

FIG. 4 compares the performance of four different ECL Assay Buffers in the ECL measurement of a labeled reagent that was immobilized on the surface of an unetched (FIG. 4A) or plasma etched (FIG. 4B) carbon ink electrode. The figure shows the signals from surface bound reagent, the background signal measured in the absence of the bound reagent and the signal to background ratio (S/B).

Figure 5A:
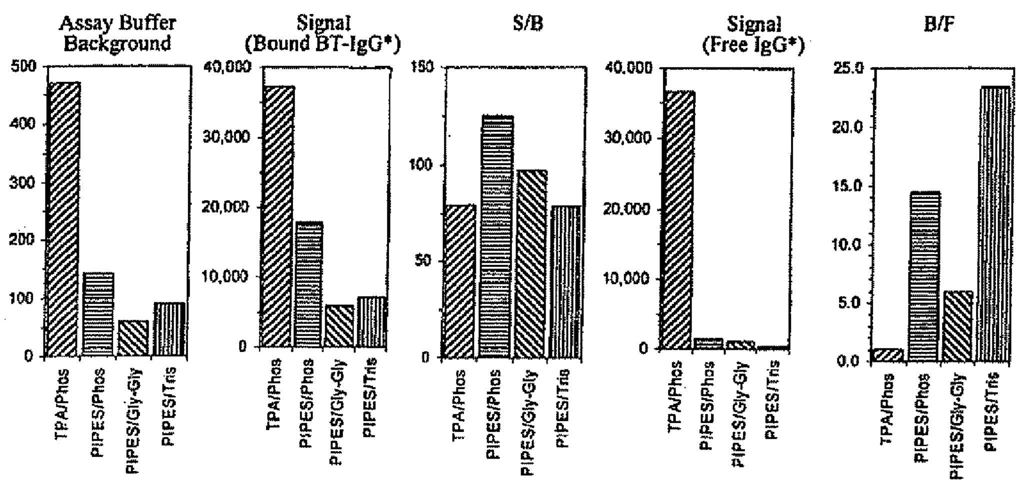
Figure 5B:
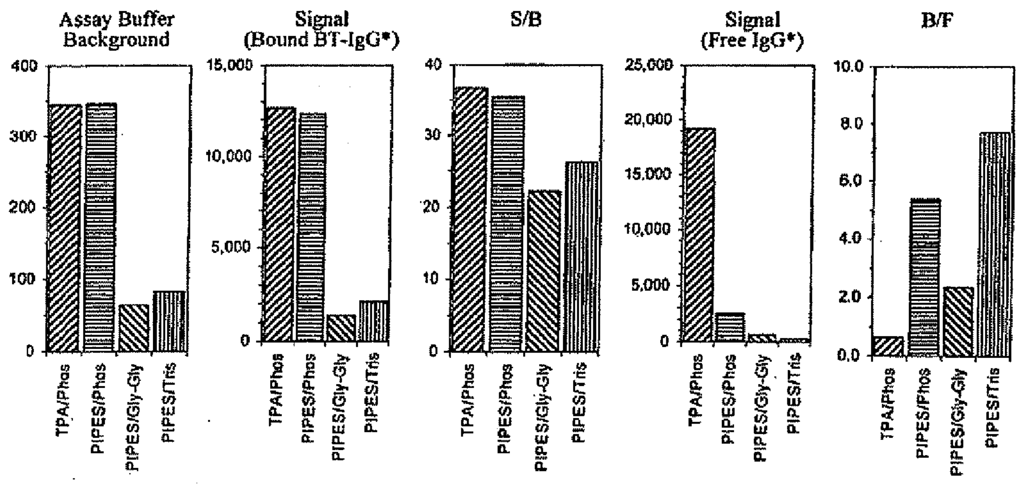

FIG. 5 compares the performance of four different ECL Assay Buffers in the ECL measurement of a labeled reagent that was immobilized on the surface of an unetched (FIG. 5A) or plasma etched (FIG. 5B) carbon ink electrode. The figure shows the signals from surface bound reagent, the background signal measured in the absence of the bound reagent and the signal to background ratio (S/B). The figure also shows the signal obtained when a non-surface bound labeled reagent was introduced into the ECL Assay Buffers and the ratio of the signals from the surface bound and non-surface bound reagents (B/F).

Figure 6A:
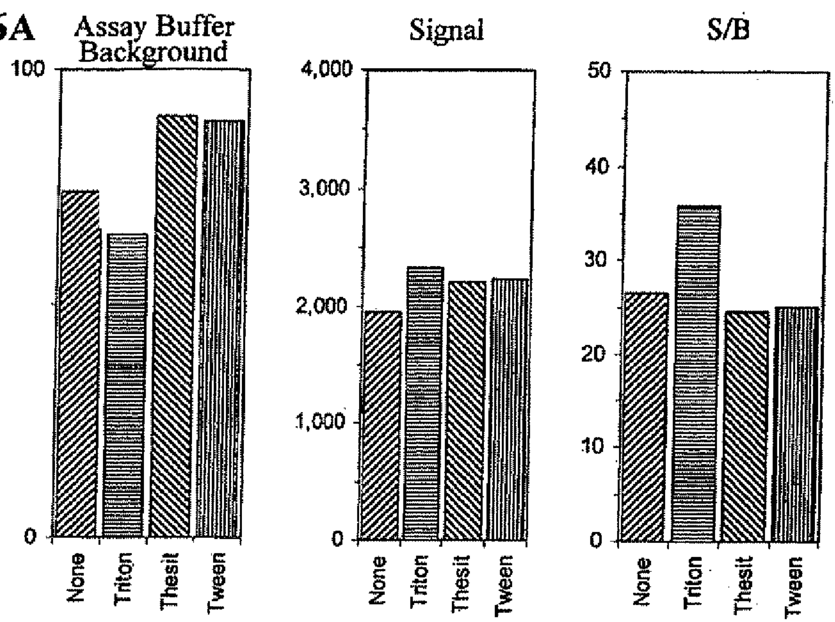
Figure 6B:
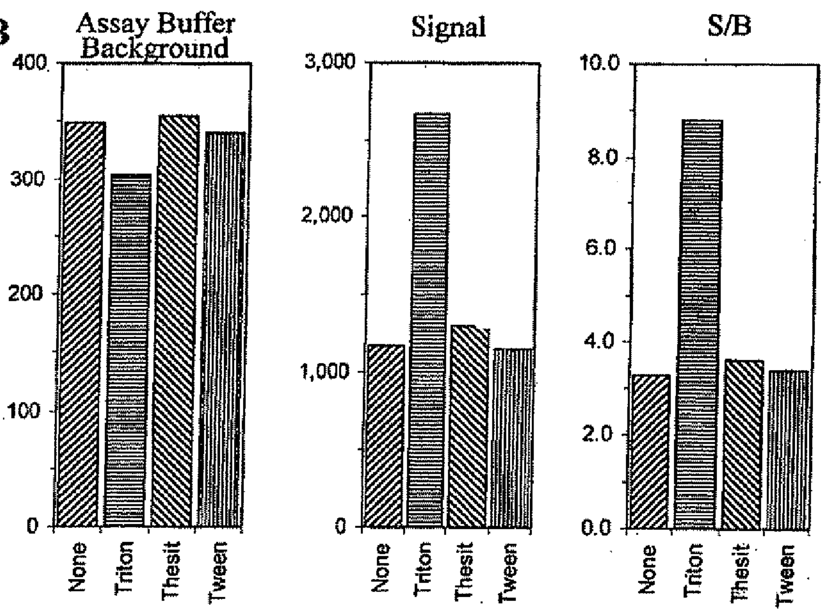

FIG. 6 compares the effect of three different detergents on the ECL signal from a labeled reagent that was immobilized on the surface of a plasma etched carbon ink electrode. The detergents were introduced into an ECL Assay Buffer comprising TPA and phosphate (FIG. 6A) or PIPES and phosphate (FIG. 6B). The figure shows the signals from surface bound reagent, the background signal measured in the absence of the bound reagent and the signal to background ratio (S/B).

Figure 7:
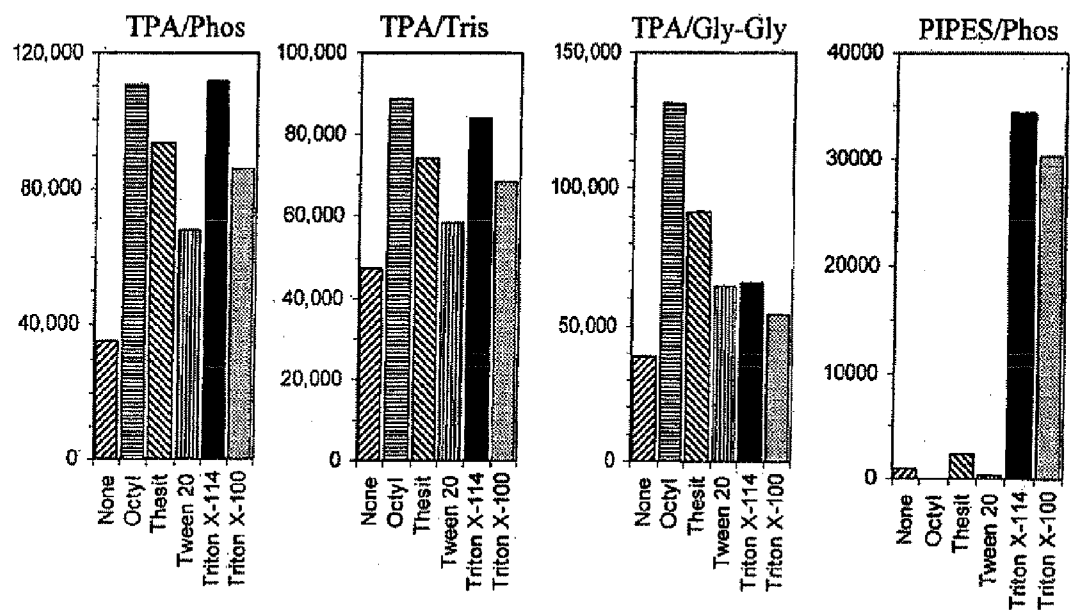

FIG. 7 compares the effect of five different detergents on the ECL signal from a labeled reagent that was immobilized on the surface of a non-etched carbon ink electrode. The detergents were introduced into four different ECL Assay Buffers differing in the identity of the ECL coreactant or pH buffering agent. The figure shows the signals from surface bound reagent, the background signal measured in the absence of the bound reagent and the signal to background ratio (S/B).

5. DETAILED DESCRIPTION OF THE INVENTION

The invention, as well as additional objects, features and advantages thereof, will be understood more fully from the following detailed description of certain preferred embodiments.

An ECL-active species may be referred to as an ECL moiety, ECL label, ECL label compound or ECL label substance, etc. It is within the scope of the invention for these ECL-active species—when utilized in certain of the composition, reagent, kit, method, or system embodiments in accordance with the invention—to be linked to other molecules and, in particular, to components of biochemical or biological assays, e.g., an analyte or an analog thereof, a binding partner of the analyte or an analog thereof, a further binding partner of such aforementioned binding partner, or a reactive component capable of binding with the analyte, an analog thereof or a binding partner as mentioned above. The above-mentioned species can also be linked to a combination of one or more binding partners and/or one or more reactive components. In certain enzymatic assays, an ECL-active species may be linked to an enzyme substrate.

It is similarly within the scope of the invention for the aforementioned "composition", hereinafter sometimes an "ECL, composition", or a "system" to contain unstable, metastable and other intermediate species formed in the course of the ECL reaction, such as an ECL moiety in an excited state as aforesaid and the above-mentioned strong reducing agent. Additionally, although the emission of visible light is an advantageous feature of certain embodiments of the invention it is within the scope of the invention for the composition (hereinafter sometimes "ECL composition") or system to emit other types of electromagnetic radiation, such as infrared or ultraviolet light, X-rays, microwaves, etc. Use of the terms "electrochemiluminescence", "electrochemiluminescent", "electrochemiluminesce", "luminescence", "luminescent" and "luminesce" in connection with the present invention does not require that the emission be light, but admits of the emission's being such other forms of electromagnetic radiation.

The present invention relates to ECL assay buffers, assay compositions containing the same, and methods of using the same. As stated above, several disadvantages were discovered when using the phosphate based ECL assay buffer of the prior art. More specifically, it was found during the development of a specific ECL assay for tyrosine kinase activity that the phosphate in a standard formulation of the ECL coreactant TPA (ORIGEN Assay Buffer, IGEN International: 200 mM Phosphate, ~100 mM TPA, pH ~7.5) disrupted the binding between an phospho-specific antibody and a phosphorylated substrate. The assay involved i) the kinase-dependent phosphorylation of a peptide immobilized on a carbon electrode; ii) the specific binding of a labeled (with a derivative of $Ru(bpy)_3$) phospho-specific antibody; iii) the addition of the ECL coreactant tripropylamine (TPA) and iv) the detection of ECL from the bound label (see, e.g., Example A below). Applicants discovered that when TPA was added by the addition of ORIGEN Assay Buffer that the measured ECL signal was sharply dependent on the time the binding complex was left exposed to the ORIGEN Assay Buffer (FIG. 1); the measured signal dropped sharply over time. In fact, after a 1-hour incubation only a small fraction (~10%) of initial signal was detected. The affinity of the pY20 antibody (Zymed Lab) used in the assay toward the phosphotyrosine sites that were formed at the surface of the plate during the enzymatic reaction was much greater than toward free phosphate in solution. However, the high concentration of free phosphate in ORIGEN assay buffer (200 mM) is now believed to have caused the dissociation of phospho-tyrosine/pY20 complex, resulting in the signal decaying sharply.

One way around this problem was to have a fixed time between the dispensing of ECL assay buffer and the read step so that the signal decay is calibrated and subtracted. However, this approach is not desirable in high throughput screening applications, where robustness of the assay and flexibility of dispensing protocol are desired.

Thus, a number of different organic pH buffers were tested as alternatives to the conventional phosphate based assay buffer. Many of the conventional biological buffers (including Tricine, HEPES, MOPS, BES—all from Sigma), however, interfered with the ECL generation from TPA and provided only 2-20% of ECL signal observed with the ORIGEN assay buffer. Applicants, however, discovered a set of buffers that provided ECL signals that were comparable to the signal observed in TPA/phosphate.

Accordingly, applicants have discovered that substitution of the phosphate buffer with a pH buffer which was substantially free of inorganic phosphate can ECL signal comparable to the signal observed in standard ORIGEN assay buffer, without the above-described disadvantages. Preferably, the pH buffer is free of inorganic buffer.

Furthermore, applicants have discovered that the phosphate-free ECL assay buffers of the invention are not only beneficial when applied to phosphopeptide binding assays but have other beneficial properties (including lower background signals) that may improve a wide range of ECL assays.

Furthermore, applicants have discovered ECL assay buffer background reducing agents that, when introduced into ECL assay buffers reduce ECL assay buffer background and improve assay performance. These agents are, preferably, also pH buffering agents, most preferably, GlyGly or Tris.

Furthermore, applicants have discovered novel ECL assay buffers that employ ECL coreactants other than the traditional TPA. Surprisingly, a number of coreactants have been discovered to generate ECL signals that are comparable to those generated with TPA. In addition, the use of ECL coreactants other than TPA have been found to improve the performance of non-washed ECL assays through their improved ability, relative to TPA, to discriminate between ECL labels that are held in proximity to an electrode and labels that are free in solution. The use of coreactants other than TPA has additional benefits due to the higher water solubility and lower vapor pressure of some of the new coreactants that have been identified.

Furthermore, applicants have discovered that the presence or absence of detergents can have profound impact on the performance of an ECL assay buffer. Surprisingly, the effect of detergents on ECL can be influenced by the choice of ECL coreactant and working electrode material. Applicants have developed detergent-containing ECL assay buffers suitable for a variety of different applications and ECL systems.

As noted above, one aspect of the invention relates to improved ECL Assay Buffers that comprise an ECL coreactant and, preferably, a pH buffering agent. The ECL Assay Buffers provide a suitable environment for efficiently inducing ECL labels to emit ECL and for sensitively measuring ECL labels via the measurement of ECL. The ECL Assay Buffers of the invention may optionally comprise additional components including detergents, preservatives, anti-foaming agents, ECL active species, salts, metal ions and/or metal chelating agents. The ECL Assay Buffers of the invention may also include components of a biological assay, which in some cases may be labeled with an ECL label, including binding reagents, enzymes, enzyme substrates, cofactors and/or enzyme inhibitors.

Preferably, the ECL assay buffers of the invention are aqueous or substantially aqueous in nature, although it may be desirable in some applications to add organic cosolvents such as DMSO, DMF, methanol, ethanol or other alcohols. In one embodiment of the invention, an ECL assay buffer (or one or more components thereof) is provided in dry form and the user forms the ECL assay buffer solution by addition of the appropriate solvent or matrix (preferably a water or an aqueous medium).

5.1 ECL Coreactants

Most, if not all, current commercial applications of ECL technology involve the measurement of ECL labels (and, in particular, organometallic complexes of ruthenium) in the presence of an ECL assay buffer containing tri-n-propylamine (TPA) as a coreactant and phosphate as a pH buffering agent. These ECL assay buffers have been optimized for and have provided excellent performance in commercial ECL instrumentation that employ, as a solid phase for binding assays, magnetic particles that are collected on the surface of a metal (typically, platinum) electrode.

Applicants have discovered that in some applications, certain functionalized tertiary alkylamines can provide performance that is comparable or better to TPA. These functionalized tertiary amines are especially useful in assays employing carbon-based electrodes (e.g., electrodes comprising carbon particle or carbon nanotubes including composite materials such as plastics and inks) and/or assay reagents (such as binding reagents) that are immobilized onto electrodes. The functionalized tertiary alkylamines of the invention, preferably, have one or more of the following properties: i) they are oxidized on carbon-based electrodes in a one electrode oxidation to give an amine radical cation which can subsequently lose a proton to form a radical reductant (Scheme 1); ii) they have an oxidation potential on carbon-based electrodes that is comparable (within 150 mV) or greater than that of $Ru(II)(bpy)_3$; iii) they can be oxidized, most preferably at a pH between 6 and 9, at a potential less than that required to breakdown water at a carbon-based electrode; iv) the energy released by the reaction of the radical reductant with Ru(III)(bpy)3 to produce Ru(II)(bpy)3 is sufficient to produce Ru(II)(bpy)3 in a luminescent excited state and v) the lifetimes of the amine radical cation and/or radical reductant are less than the corresponding TPA-derived species.

Scheme I.

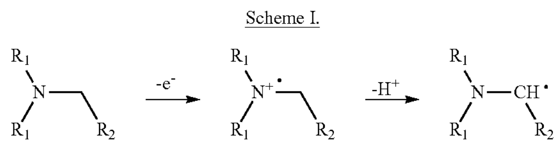

Applicants have discovered that, through the use of the functionalized tertiary alkylamines of the invention, it is possible to improve the selectivity of ECL excitation at an electrode for ECL labels bound to the electrode (as opposed to ECL labels that are free in solution). Without being bound by theory, it is believed that this increased selectivity is due to the lower lifetimes of the amine radical cation and/or radical reductant relative to the corresponding TPA-derived species (thus limiting the participation of the reactive species to ECL reactions that occur proximate to the electrode surface). Preferably, the diffusion distance of the amine radical cation and/or radical reductant (the distance that the species can diffuse during its lifetime) is less than 1 μm, more preferably, <500 nm, even more preferably less than 100 nm, even more preferably less than 50 nm and most preferably <10 nm. The high selectivity between free and bound labels has led to improved sensitivity in non-washed ECL assay formats. The ratio of signal from bound label and free label (B/F ratio) may improved by replacing TPA with a non-TPA coreactant of the invention. This improvement is preferably greater than a factor of 2, more preferably greater than a factor of 5 and most preferably greater than a factor of 10.

The functionalized tertiary amine coreactants of the invention, preferably have the structure $NR^1R^2R^3$, wherein $R^1$, $R^2$ and $R^3$ are alkyl groups comprising at least 2, preferably 3, carbons and wherein one or more of $R^1$, $R^2$ and $R^3$ are functionalized with a hydrophilic functional group, more preferably a charged group, most preferably a negatively charge group. Preferred functional groups include hydroxyl, dialkylamino, sulfate, sulfonate, carboxylate and carboxylic acid ester.

Especially preferred coreactants include compounds with the structure $(n\text{-}Pr)_2N(CH_2)_nR$, wherein n is greater than or equal to 2 (more preferably 3), and R is a hydrophilic functional group as defined above, preferably, carboxylate, dialkylamino (more preferably dipropylamino) or most preferably sulfonate.

Other preferred coreactants include compounds with the structure

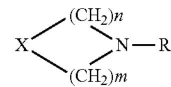

Wherein i) X is —$(CH_2)$— or a heteroatom, preferably —O—, —S—, or —$N(R^1)$—; ii) R and $R^1$ are alkyl groups comprising 2 or more (preferably 3 or more) carbons; iii) n and m are each greater than or equal to 1 and are preferably two and iv) R (and, optionally $R^1$) comprise a hydrophilic functional group as defined above. Most preferably, R is —$(CH_2)_n$—$F^1$, wherein n is greater than or equal to 3 and $F^1$ is a hydrophilic functional group, preferably, carboxylate or sulfonate. In the cases where X is —$N(R^1)$—, $R^1$ is, most preferably, —$(CH2)_n$-$F^2$, wherein n is greater than or equal to 3 and $F^1$ is H, alkyl, or a hydrophilic functional group, most preferably, carboxylate or sulfonate.

Many of the so-called "Good" buffers (Good et al., Biochemistry, 5, 467 (1966); Good et al., Methods in Enzymol., 24, Part B, 53 (1972) and Ferguson et al., Anal. Biochem., 104, 300 (1980)) have tertiary amines and have been found to act as ECL coreactants on carbon electrodes. These "Good" buffers, generally have tertiary amines having piperazine or morpholine cores. Specific amines that act as ECL coreactants on carbon-based electrodes include: 3-(di-n-propylamino)-propanesulfonic acid; 4-(di-n-propylamino)-butanesulfonic acid; 4-[bis-(2-hydroxyethane)-amino]-butanesulfonic acid; piperidine-N-(3-propanesulfonic acid); azepane-N-(3-propanesulfonic acid); piperidine-N-(3-propionic acid) (PPA); 3-morpholino-2-hydroxypropanesulfonic acid (MOPSO); 3-morpholinepropanesulfonic acid (MOPS); N-(2-hydroxyethyl)piperazine-N'-3-propanesulfonic acid (EPPS); N-(2-hydroxyethyl) piperazine-N'-3-ethanesulfonic acid (BES); piperazine-N,N'-bis(2-ethanesulfonic acid) (PIPES); triethanolamine; N-2-hydroxypiperazine-N-2-ethanesulfonic acid (HEPES); piperazine-N,N'-bis-4-butanesulfonic acid; homopiperidine-N-3-propanesulfonic acid; piperazine-N,N'-bis-3-propanesulfonic acid; piperidine-N-3-propanesulfonic acid; piperazine-N-2-hydroxyethane-N'-3-methylpropanoate; piperazine-N,N'-bis-3-methylpropanoate; 1,6-diaminohexane-N,N,N',N'-tetraacetic acid; N,N-bis propyl-N-4-aminobutanesulfonic acid; N-tris(hydroxymethyl)methyl-2-aminoethane sulfonic acid (TES); 1,3-bis[tris (hydroxymethyl)methylamino]propane (bis-Tris propane); 3-dimethylamino-1-propanol; 3-dimethylamino-2-propanol; N,N,N',N'-tetrapropylpropane-1,3-diamine (TPA dimer); piperazine-N,N'-bis(2-hydroxypropane)sulfonic acid (POPSO) and 2-hydroxy-3-[4-(2-hydroxyethyl)piperazin-1-yl]propane-1-sulfonic acid (HEPPSO). HEPES. POPSO, HEPPSO, EPPSO, PPA and PIPES are especially preferred for their high signals and high discrimination between bound and free labels. TES is also preferred for its high signal.

Additional coreactants include proline, peptides having an N-terminal proline. Preferably, the proline is N-alkylated to form a tertiary amine.

The use of coreactants having hydrophilic functional groups (and, in particular, coreactants that are zwitterionic at neutral pH) has a variety of advantages that are unrelated to their ability to act as ECL coreactants. These species tend to be highly water soluble and to have low vapor pressure. For these reasons it is possible to produce highly concentrated stock solutions that may be diluted as necessary for use. It is also possible prepare dried reagents comprising the coreactants without uncertainty due to loss of coreactant in the vapor phase. Furthermore, when present in dried reagents, these coreactants resolubilize quickly in a minimum of volume.

5.2 pH Buffering Agents

Conventional ECL assay buffers optimized for use with commercial ECL instruments have typically comprised TPA in a phosphate-based pH buffer. These formulations have been especially useful for conducting solid phase assays employing magnetic particles that are captured on an electrode. Applicants have discovered that in some applications, other pH buffering agents (including organic pH buffers) can provide performance that is comparable or better to phosphate. These non-phosphate pH buffers (and pH buffer solutions and ECL assay buffers comprising these buffers are especially useful in assays employing carbon-based electrodes (e.g., electrodes comprising carbon particle or carbon nanotubes including composite materials such as plastics and inks) and/or assay reagents (such as binding reagents) that are immobilized onto electrodes. They are also advantageous for use in assays where phosphate is an interferent. Preferably, ECL assay buffers employing the non-phosphate buffers of the invention have less than 15 mM inorganic phosphate, more preferably they have less than 5 mM inorganic phosphate, even more preferably they have less than 1 mM phosphate, even more preferably they are substantially free of inorganic phosphate, most preferably they are free of inorganic phosphate.

The pH buffering agent, preferably, is not oxidized under the conditions used to generate ECL and do not interfere with the generation of ECL. Two pH buffers that have proved especially useful are tris-(hydroxymethyl)aminomethane (Tris) and oligo(glycines), preferably glycyl-glycine (Gly-Gly). Applicants have discovered that ECL assays on carbon-based electrodes using TPA/Tris or TPA/Gly-Gly ECL assay buffers have comparable signals from electrode-bound ECL labels as those observed with conventional TPA/phosphate buffers. The background signals in the absence of ECL labels, however, are considerably less with the Tris and Gly-Gly buffers. This reduction in the background signal leads to an increase in the ratio of signal to background (S/B) and an increase in the sensitivity of ECL assays using the new formulations. Preferably, the ECL assay buffers of the invention have S/B ratios that are 2-fold, more preferably 5-fold and, most preferably, 10-fold better than those obtained using phosphate-based systems.

Without being bound by theory, applicants hypothesize that the improved performance of the Tris and Gly-gly based ECL assay buffers is related to an ability of the buffering agents to act as ECL assay buffer reducing agents by reacting with and destroying tertiary amine oxidation products and/or other reactive oxidized species (e.g., amine radical cations and radical reductants) that are responsible for the assay buffer background. This effect is most pronounced away from the electrode surface where the concentration of these species are lower, so the Tris and Gly-gly components do not affect signals from electrode-bound labels. The Tris and Gly-gly buffers may also improve the observed bound to free ratios, although this effect is less than that observed by switching to non-TPA buffers such as PIPES.

Applicants have found that the Tris and Gly-gly buffering systems are also suitable for use with non-TPA coreactants such as PIPES. When using coreactants such as PIPES that may act as pH buffers, it may be possible to omit additional buffering agents.

5.3 Detergents

Applicants have discovered that the presence or absence of detergents can have a surprisingly large effect on ECL signals. The nature of this effect is, unexpectedly, dependent on the electrode. On oxidized electrodes (e.g., plasma-oxidized carbon inks or plasma oxidized polymer composites containing carbon particles or carbon nanotubes) exposed to TPA-containing ECL assay buffers, the effect appears to be relatively small except in the case of phenyl ether containing detergents such as the Triton and Nonidet series of detergents (e.g., Triton X-100). A common method for generating ECL is through the use of a ramp potential. In general a plot of ECL intensity vs. applied potential has the form of a peak. ECL increases as the oxidation potentials of the label and coreactant are approached. On scanning past this potential, the ECL intensity eventually begins to drop as the coreactant is consumed and water oxidation begins to occur. Applicants have observed that the addition of phenyl ether containing detergents leads to the addition of a small ECL peak at higher potential than the main ECL peak. This peak occurs at a potential similar to the an oxidation wave observed with pure Triton X-100, thus leading applicants to speculate that the new peak is associated with the oxidation of the detergent (or an associated impurity) and the participation of the oxidation products in an ECL reaction.

The behavior on non-oxidized carbon-based electrodes (and, in particular, untreated carbon ink electrodes) is very different. On these electrodes the ECL signal in the presence of TPA-containing buffers (as well as the S/B ratio) is drastically improved by the addition of detergent. This effect appears to be relatively independent of the nature of the detergent (although non-ionic detergents are preferred due to their relatively weak ability to denature biological systems), but requires the concentration of detergent to be roughly equal to or greater than the critical micellar concentration (cmc) of the detergent. In preferred embodiments of the invention, the addition of detergent to an ECL assay buffer leads to an improvement in assay signal or S/B (preferably induced with a carbon-based electrode, most preferably a carbon-ink electrode) of greater than a factor of 2, more preferably greater than a factor of 5 and most preferably greater than a factor of 10.

The behavior of non-TPA containing ECL assay buffers and, in particular, non-TPA containing ECL assay buffers (especially, buffers comprising the non-TPA tertiary amine coreactants of the invention, preferably comprising N-substituted morpholines or piperazines, most preferably comprising PIPES) appears to be less dependent on the nature of a carbon electrode. For example, applicants have found that assays involving the use of PIPES as a coreactant, on both oxidized and non-oxidized electrodes, are unexpectedly and significantly improved by the addition of phenyl ether containing substances, and, in particular, phenyl ether containing detergents. Other detergents that did not possess the phenyl ether moiety did not produce this effect. In preferred embodiments of the invention, the addition of detergent to a non-TPA based ECL assay buffer (preferably, a PIPES-based ECL assay buffer) leads to an improvement in assay signal or S/B (preferably induced with a carbon-based electrode, most preferably a carbon-ink electrode) of greater than a factor of 10, more preferably greater than a factor of 30 and most preferably greater than a factor of 100.

In certain assays, e.g., assays involving detergent sensitive components such as biological membranes, it may be advantageous to reduce (e.g., to <0.1%) or eliminate detergents from ECL Assay Buffers. It should be understood that the various detergent containing formulations of the invention may also be prepared in low detergent or detergent-free forms for these detergent sensitive applications. In preferred embodiments, assays employing detergent sensitive components employ ECL Assay Buffers containing one of the following coreactants: TPA, N,N-bis-(hydroxyethyl)-N-4-aminobutanesulfonic acid, or $A_2N—(CH_2)_n—NB_2$, where A and B are alkyl groups (preferably, propyl) and n is an integer (preferably 3 or 4, most preferably, 3).

5.4 Preservatives

It may be beneficial when storing ECL assay buffers to include a preservative that prevents microbial growth. Preferably, the preservative has little or no effect on ECL generated using the ECL assay buffer, especially when using the ECL assay buffer on a carbon based electrode. Azide has been found to be a suitable preservative. Isothiazolones (e.g., Kathon, 2-methyl-4-isothiazolin-3-one and 5-chloro-2-methyl-4-isothiazolin-3-one), oxazolidines (e.g., Oxaban A or 4,4 dimethyl oxazolidine) and related preservatives are especially preferred due their compatibility with ECL, their high activity and the low degree of problems associated with safety hazards or environmental concerns.

5.5 Anti-Foam Agents

It may be beneficial, especially in HTS applications, to avoid the production of bubbles or foam. For this reason it may be desirable to add anti-foaming agents to ECL assay buffers. Applicants have found that many commercial anti-foaming agents (including Antifoams o-30, Antifoam 204, Antifoam A, Antifoam SE-15, Antifoam SO-25 and Antifoam 289) may be added to ECL assay buffers without significantly affecting the performance of the ECL assay buffers.

5.6 ECL Labels

The compositions of the invention may include ECL labels. The ECL labels may be conventional ECL labels. Examples of ECL labels include: i) organometallic compounds where the metal is selected from, for example, the noble metals of group VIII, including Ru-containing and Os-containing organometallic compounds such as the tris-bipyridyl-ruthenium (RuBpy) moiety and ii) luminol and related compounds. Preferably, the ECL labels are capable of repeatedly emitting electrochemiluminescence. Preferred ECL labels are ruthenium or osmium-containing organometallic species. More preferably, these ruthenium or osmium-containing organometallic comprise ruthenium or osmium chelated to polypyridyl ligands (most preferably, bipyridine, phenanthroline, and/or substituted derivatives thereof). Most preferably, the ECL labels comprise ruthenium-tris-bipyridine, the bipyridine ligands being, optionally substituted, e.g., with a linking group for attaching the label to an assay reagent.

The ECL label may be linked to an assay reagent, optionally through a linking group. Examples of binding reagents that may be linked to an ECL label include: whole cells, cell surface antigens, subcellular particles (e.g., organelles or membrane fragments), viruses, prions, dust mites or fragments thereof, viroids, antibodies, antigens, haptens, fatty acids, nucleic acids (and synthetic analogs), proteins (and synthetic analogs), lipoproteins, polysaccharides, inhibitors, cofactors, haptens, cell receptors, receptor ligands, lipopolysaccharides, glycoproteins, peptides, polypeptides, enzymes, enzyme substrates, enzyme products, second messengers, cellular metabolites, hormones, pharmacological agents, synthetic organic molecules, organometallic molecules, tranquilizers, barbiturates, alkaloids, steroids, vitamins, amino acids, sugars, lectins, recombinant or derived proteins, biotin, avidin, streptavidin. The assay reagents are preferably useful as binding reagents or enzyme substrates in, e.g., binding assays or enzyme assays.

5.7 Compositions

One aspect of the invention relates to compositions comprising the ECL assay buffers of the invention.

Another aspect of the present invention relates to compositions suitable for use in an assay comprising a pH buffer substantially free of inorganic phosphate. Suitable pH buffers include glycylglycine ("Glygly"), tris(hydroxymethyl) aminomethane ("Tris") or combinations thereof. Other pH buffers which are also substantially free of or do not contain inorganic phosphate would also be suitable for use in the invention.

According to one embodiment of the invention, the composition comprises a pH buffer, wherein the composition is, preferably, substantially free of inorganic phosphate and, preferably further comprises one or more ECL co-reactants (preferably, TPA or alternatively, a non-TPA coreactant, more preferably an N-substituted morpholine or piperazine, most preferably PIPES). According to a particularly preferred embodiment, the composition is free of inorganic phosphate. Suitable pH buffers include glygly and tris. Additional buffers may be selected on the basis of certain preferred characteristics: i) the ability to buffer in the pH range of 6.5-8.5, preferably 7-8 (more preferably, the pKa of the buffer is in the range of 6.5 to 8.5 or more preferably, from 7.5 to 8.5); ii) commercial availability at low cost; iii) the lack of an inhibitory effect on ECL and/or iv) the lack of a significant oxidation wave in the range of 0-1.2 V or more preferably 0-1.5 V (the voltage window for the oxidation of $Ru(bpy)_3$ and TPA).

According to another embodiment of the invention, the composition comprises a non-phosphate pH buffering agent and, preferably further comprises one or more ECL co-reactants (preferably, TPA or alternatively, a non-TPA coreactant, more preferably an N-substituted morpholine or piperazine, most preferably PIPES). Preferably, the composition has less than 15 mM inorganic phosphate, more preferably it has less than 5 mM inorganic phosphate, even more preferably it has less than 1 mM phosphate, even more preferably it is substantially free of inorganic phosphate, most preferably it is free of inorganic phosphate. Suitable pH buffers include glygly and tris. Additional buffers may be selected on the basis of certain preferred characteristics: i) the ability to buffer in the pH range of 6.5-8.5, preferably 7-8 (more preferably, the pKa of the buffer is in the range of 6.5 to 8.5 or more preferably, from 7.5 to 8.5); ii) commercial availability at low cost; iii) the lack of an inhibitory effect on ECL and/or iv) the lack of a significant oxidation wave in the range of 0-1.2 V or more preferably 0-1.5 V (the voltage window for the oxidation of $Ru(bpy)_3$ and TPA).

Preferably, the ECL co-reactant used in these embodiments is suitable for use in an electrode induced luminescence reaction (e.g., electrochemiluminescence). Suitable ECL co-reactants include tripropylamine (TPA). Non-TPA coreactants (preferably, tertiary amines other than TPA as described in the coreactants section above) may be advantageous in some applications, in particular, in non-washed assay formats.

Preferably, the composition comprises between 10 and 2000 mM pH buffer, more preferably 50 and 1200 mM, even more preferably between 100 and 600 mM, and most preferably between 300 and 500 mM.

Preferably, the composition comprises between 10 and 1000 mM, ECL co-reactant, more preferably 30 and 600 mM, even more preferably between 50 and 200 mM, and most preferably between 75 and 150 mM.

The optimal range of TPA concentrations in the pH buffers containing Tris and Gly-Gly is very similar to concentrations of ORIGEN® buffer (i.e., ranging from 50-200 mM). The tested range of concentrations of Tris and Gly-Gly buffers is 100-600 mM. Preferably, the concentration is 200 mM. ECL assay buffers comprising non-TPA coreactants of the invention (preferably, PIPES) may include similar ranges of coreactant concentrations, although in many applications the preferred range is 10-100 mM, most preferably 20-50 mM.

According to another preferred embodiment, the final formulation of the Gly-Gly/TPA buffer is: 200 mM Gly-Gly, 100 mM TPA, 0.1% Triton at pH=7.8±0.05.

According to another preferred embodiment, the final formulation of the Gly-Gly/TPA buffer is: 50-1000 mM Gly-Gly, 50-1000 mM TPA, at pH=7.8±1. Preferably, the formulation also comprises 0.2%-2% Triton X-100 and/or 20-500 mM salt.

According to another preferred embodiment, the final formulation for the Tris/TPA buffer is: 200 mM Tris, 100 mM TPA, 0.1% Triton at pH=7.8±0.05.

According to another preferred embodiment, the final formulation for the Tris/TPA buffer is: 50-1000 mM Tris, 50-1000 mM TPA, at pH=7.8±0.05. Preferably, the formulation also comprises 0.2%-2% Triton X-100. and/or 20-500 mM salt.

According to another preferred embodiment, the final formulation for the PIPES/Phos buffer is: 40-1000 mM phosphate (preferably, potassium phosphate), 10-200 mM PIPES, at pH=7.8±0.05. Preferably, the formulation also comprises 0.2%-2% Triton X-100.

Using Tris and Gly-Gly assay buffers significantly improved the stability of phosphopeptide-anti-phosphopeptide complexes in ECL-based Tyrosine Kinase assays. However, some dissociation of the complexes was observed in Tris buffer, although at much slower rates than in ORIGEN assay buffer. In the case of the Gly-Gly buffer, ECL signal slowly increased, because no stop reagent was introduced into assay solution to quench the enzymatic reaction.

According to one preferred embodiment, the composition further comprises a stop reagent (i.e., a reagent added to stop a reaction or reduce interference with a reaction). Chelating agents such as ethylenediaminetetraacetic acid (EDTA) are common stop reagents in Mg-dependent kinase assays. EDTA binds $Mg^{2+}$ ions that are require for successful activation of ATP. The addition of 5 mM EDTA into Gly-Gly assay buffer, for example, helps to stop residual tyrosine kinase enzymatic activity. Dissociation of phosphopeptide-anti-phosphopeptide complexes in Gly-Gly/TPA buffer with 5 mM EDTA does not exceed 1% per 1 hour in a non-washed assay format. At concentrations higher than 10 mM, EDTA may have a negative effect on absolute value of ECL signal, but does not compromise stability of ECL signal upon incubation in assay buffer. Depending on desired final read volume in 96-well plates (100 μl or 250 μl) and the type of assay (washed or non-washed) formulation of Gly-Gly/TPA solution may be different.

Preferably, the composition has a pH ranging from 6 to 9, more preferably from 7 to 8, even more preferably from 7.5 to 8 and most preferably about 7.8. According to one preferred embodiment, the pH is adjusted by addition of an acid or base, preferably KOH, more preferably 10% KOH.

One embodiment of the invention relates to an ECL assay buffer comprising:

(a) glycylglycine (Gly-Gly), preferably from 0.1 to 0.7 M, more preferably 0.3 and 0.5 M, and most preferred about 0.2 M; and (b) tripropylamine (TPA), preferably from 0.01 M to 0.3 M, more preferably 0.05 to 0.2, and most preferred about 0.1 M.

Preferably, the assay buffer further comprises EDTA (preferably 1 to 10 mM, more preferably 5 mM). Preferably, the assay buffer has a pH ranging from 6 to 9, more preferably from 7 to 8, even more preferably from 7.5 to 8 and most preferably about 7.8. According to one preferred embodiment, the pH is adjusted by addition of an acid or base, preferably KOH, more preferably 10% KOH.

Another preferred embodiment of the invention relates to an ECL assay buffer comprising:

(a) tris[hydroxymethyl)aminomethane (Tris), preferably from 0.1 to 0.7 M, more preferably 0.3 to 0.5 M and most preferred about 0.2 M; and (b) tripropylamine (TPA), preferably from 0.01 M to 0.3 M, more preferably from 0.05 to 0.2 M and most preferred about 0.1 M.

Preferably, the assay buffer further comprises ethylenediaminetetraacetic acid (EDTA), preferably 1 to 10 mM, more preferably 5 mM. Preferably, the composition has a pH ranging from 6 to 9, more preferably from 7 to 8, even more preferably from 7.5 to 8 and most preferably about 7.8. According to one preferred embodiment, the pH is adjusted by addition of an acid or base, preferably KOH, more preferably 10% KOH.

Another preferred embodiment of the invention relates to ECL assay buffers comprising coreactants other than TPA, preferably trialkylamines presenting hydrophilic functional groups (as described in the coreactants section). Preferably the coreactant is PPA or PIPES, most preferably PIPES. The concentration of coreactant is, preferably, between 10 and 800 mM, most preferably between 10 and 200 mM, most preferably between 20 and 50 mM. Preferably, the ECL assay buffer also comprises a pH buffering agent, preferably, phosphate, Tris or Gly-Gly. The concentration of the pH buffering agent is preferably between 0 and 800 mM, more preferably between 0 and 400 mM, even more preferably between 20 and 200 mM and most preferably between 75 and 150 mM. Preferably, the composition has a pH ranging from 6 to 9, more preferably from 7 to 8, even more preferably from 7.2 to 7.8 and most preferably about 7.5. Preferably, the ECL assay buffer also includes a substance with a phenyl ether moiety and/or a detergent, preferably a non-ionic detergent, even more preferably a phenyl ether containing detergent, most preferably Triton X-100. Preferably the concentration of detergent is greater than 0.02%, more preferably greater than 0.05%, most preferably between 0.05 and 0.5%.

According to one preferred embodiment, the reagents or compositions of the invention further comprise one or more detergents and/or surfactants (e.g., classes of non-ionic detergents/surfactants known by the trade names of Nonidet, Brij, Triton, Tween, Thesit, Lubrol, Genapol, Pluronic, Tetronic, F108, and Span). Especially preferred detergents include: Tween 20, Triton X-100, NP-40 and Thesit.

Another preferred embodiment of the invention relates to reagent compositions comprising the assay buffers described above in concentrated form. Preferably, the reagent compositions can be diluted, preferably with an aqueous solution, to result in an assay buffer having the optimal concentration of ingredients for use in an assay, preferably an ECL assay.

Another embodiment relates a dry reagent precursor comprising one of the above described assay buffers in dry form. Preferably, the dry reagent precursor can be combined with a solution, preferably with an aqueous solution, to result in an assay buffer solution having the optimal concentration of ingredients for use in an assay, preferably an ECL assay.

Another aspect of the invention relates to a reagent containing one or more pH buffers substantially free of inorganic phosphate suitable for use in providing a composition for conducting an assay, preferably a luminescence assay, more preferably a chemiluminescence assay or an electrode induced luminescence assay, and most preferred an electrochemiluminescence assay.

Another aspect of the invention relates to a reagent containing one or more ECL assay background reducing agents (preferably, non-phosphate pH buffering agents) suitable for use in providing a composition for conducting an assay, preferably a luminescence assay, more preferably a chemiluminescence assay or an electrode induced luminescence assay, and most preferred an electrochemiluminescence assay. Preferably, the reagent has less than 15 mM inorganic phosphate, more preferably it has less than 5 mM inorganic phosphate, even more preferably it has less than 1 mM phosphate, even more preferably it is substantially free of inorganic phosphate, and most preferably it is free of inorganic phosphate.

According to one embodiment, the reagent comprises an ECL assay buffer reducing agent (preferably, a non-phosphate pH buffering agent) and/or is substantially free of inorganic phosphate, and the reagent is suitable for use in providing a composition for conducting an ECL assay wherein electromagnetic radiation is emitted by an assay composition comprising members selected from the group consisting of:

(i) a metal-containing ECL moiety capable of being converted to an excited state from which electromagnetic radiation;

(ii) an ECL co-reactant (preferably an amine or an amine moiety, most preferably a tertiary amine, most preferably TPA) which when oxidized forms a strong reducing agent; and (iii) an electrolyte capable of functioning as a medium in which said ECL moiety and said ECL co-reactant can be oxidized.

Preferably, said reagent comprises said pH buffer, said ECL co-reactant and one of the other two members of said group (i)-(iii).

Another aspect of the invention relates to assay compositions comprising one or more binding reagents, enzymes and/or substrates and the pH buffer of the invention.

Another aspect of the invention relates to compositions, reagents, kits and methods for carrying out protein kinase and phosphorylase assays and/or for measuring phospho-peptides, phospho-proteins, and phospho-amino acids. One embodiment of the invention relates to a composition comprising a pH buffer and a phospho-peptide specific antibody, where the composition is substantially free of inorganic phosphate. Preferably, the composition is free of inorganic phosphate. Preferably, the composition further comprises a phosphopeptide, phosphoamino acid and/or phosphylated protein that binds the phospho-peptide specific antibody.

Preferably, the pH buffer is selected from the group consisting of glycylglycine, tris[hydroxymethyl)aminomethane or combinations thereof.

Preferably, the composition further comprises one or more components selected from the group consisting of kinases and kinase substrate. According to another embodiment, the compositions comprise or one or more components selected from the group consisting of phosphatase and phosphatase substrate.

Preferably, the composition has a pH between 6 to 9, preferably between 7 to 8, more preferably from 7.5 to 8, and most preferred about 7.8.

According to one preferred embodiment, the composition further comprises one or more ECL co-reactants. Preferably, the ECL co-reactant comprises an amine or an amine moiety. More preferably, the ECL co-reactant comprises tripropylamine (TPA).

According to another preferred embodiment, the composition further comprises a stop reagent. Preferably, the stop reagent comprises ethylenediaminetetraacetic acid (EDTA).

According to another preferred embodiment, the composition further comprises an acid or base, preferably KOH.

According to one preferred embodiment, the reagents or compositions of the invention further comprises one or more detergents and/or surfactants (e.g., classes of non-ionic detergents/surfactants known by the trade names of Brij, Triton, Tween, Thesit, Lubrol, Genapol, Pluronic, Tetronic, F108, and Span).

Preferably, the composition comprises an inhibitor and/or an enzyme, more preferably an inhibitor to and/or an enzyme for a phosphorylating or dephosphorylating reaction.

Another embodiment of the invention relates to a composition comprising a pH buffer and an ECL co-reactant, said composition being substantially free of inorganic phosphate. Preferably, the composition is free of inorganic phosphate.

Preferably, the pH buffer is selected from the group consisting of glycylglycine, tris[hydroxymethyl)aminomethane or combinations thereof.

Preferably, the composition comprises one or more components selected from the group consisting of kinases and kinase substrate or one or more components selected from the group consisting of phosphatase and phosphatase substrate.

Preferably, the composition has a pH between 6 to 9, preferably between 7 to 8, more preferably from 7.5 to 8, and most preferred about 7.8.

Preferably, the ECL co-reactant comprises an amine or an amine moiety. More preferably, the ECL co-reactant comprises tripropylamine (TPA).

According to another preferred embodiment, the composition further comprises a stop reagent. Preferably, the stop reagent comprises ethylenediaminetetraacetic acid (EDTA).

According to another preferred embodiment, the composition further comprises an acid or base, preferably KOH.

Preferably, the composition comprises an inhibitor and/or an enzyme, more preferably an inhibitor to and/or an enzyme for a phosphorylating or dephosphorylating reaction.

According to one preferred embodiment, the pH buffer is glycylglycine and said composition further comprises ethylenediaminetetraacetic acid (EDTA) and TPA. Preferably, the composition also further comprises KOH and/or an ECL moiety.

Another embodiment of the invention relates to a reagent comprising a pH buffer, wherein said pH buffer is substantially free of inorganic phosphate and said reagent is suitable for use in providing a composition for conducting an ECL assay wherein electromagnetic radiation is emitted by an assay composition comprising members selected from the group consisting of:

(i) a metal-containing ECL moiety capable of being converted to an excited state from which electromagnetic radiation is emitted;

(ii) an ECL co-reactant which when oxidized forms a strong reducing agent; and (iii) an electrolyte capable of functioning as a medium in which said ECL moiety and said amine or amine moiety can be oxidized.

Preferably, the reagent further comprises said pH buffer, the ECL co-reactant (preferably an amine or amine moiety) and one of the other two members of said group (i)-(iii).

Another embodiment of the invention relates to a reagent comprising a pH buffer, wherein said pH buffer is substantially free of inorganic phosphate and said reagent is suitable for use in providing a composition for conducting an ECL assay wherein electromagnetic radiation is emitted by an assay composition comprising members selected from the group consisting of:

(i) a metal-containing ECL moiety capable of being converted to an excited state from which electromagnetic radiation is emitted;

(ii) an ECL co-reactant which when oxidized forms a strong reducing agent, wherein said ECL co-reactants is an amine or an amine moiety (preferably TPA); and (iii) an electrolyte capable of functioning as a medium in which said ECL moiety and said amine or amine moiety can be oxidized.

Another embodiment of the invention relates to a composition comprising:

(a) a phospho-specific antibody;

(b) a reagent selected from the group consisting of phosphorylating enzyme, a substrate to a phosphorylating enzyme or combinations thereof; and (b) a pH buffer, where the composition is substantially free of, preferably free of inorganic phosphate.

Preferably, the composition also comprises an ECL co-reactant (e.g., TPA).

5.8 Kits

One aspect of the invention relates to kits comprising, in one or more containers, one or more components of the ECL assay buffers of the invention. These components may be combined, optionally with additional reagents, to form the ECL assay buffers of the invention. The kits may also comprise additional assay related components such as ECL labels, ECL labeled assay reagents, enzymes, binding reagents, electrodes, assay plates, etc.

Another aspect of the invention relates to kits containing, in one or more containers, one or more ECL assay buffers that contain a trialkylamine coreactant of the invention other than TPA. Preferably, the kit is contained in one or more glass or plastic containers, appropriately labeled with information regarding the buffer contents and instructions regarding proper storage and use in assay. Some or all of the components of the ECL assay buffer may be stored in a dry state. The kits may further comprise other assay related components such as enzymes, binding reagents, electrodes, assay plates, etc.

Another aspect of the invention relates to kits containing, in one or more containers, one or more ECL assay buffers that are substantially free of inorganic phosphate and/or comprise ECL assay buffer reducing agents (preferably, non-phosphate pH buffering agents). Preferably, the kit is contained in one or more glass or plastic containers, appropriately labeled with information regarding the buffer contents and instructions regarding proper storage and use in assay. Some or all of the components of the ECL assay buffer may be stored in a dry state. The kits may further comprise other assay related components such as ECL labels, ECL labeled assay reagents, enzymes, binding reagents, electrodes, assay plates, etc.

No formal study on shelf-life stability of Gly-Gly/TPA buffer has been performed. However, using 3-4 month old assay buffer did not affect assay performance. Applicants believe that the same precautions should be used for Gly-Gly stability, for example, as for ORIGEN assay buffer. Preferably, concentrations of divalent ions in the solution are kept below the μM level.

Preferably, the kit is adapted or suitable for performing an ECL assay wherein electromagnetic radiation emitted by a composition is detected, which kit contains, in one or more containers, a pH buffer and the kit is, preferably, substantially free of inorganic phosphate and/or comprises an ECL assay buffer reducing agent (preferably, a non-phosphate pH buffering agent). This kit also comprises at least one other component selected from the group consisting of: (i) a metal-containing ECL moiety capable of being converted to an excited state from which electromagnetic radiation is emitted; (ii) an ECL co-reactant (preferably an amine or an amine moiety) which when oxidized forms a strong reducing agent; and (iii) an electrolyte capable of functioning as a medium in which said ECL moiety and said ECL co-reactant (e.g., amine or amine moiety) can be oxidized, said kit comprising at least one separate component in which one or more members of the group consisting of said ECL moiety (i), ECL co-reactant (ii), and electrolyte (iii) is included.

Another aspect of the invention relates to kits for use in conducting assays, preferably luminescence assays, more preferably electrode induced luminescence assays, and most preferably electrochemiluminescence assays, comprising, in one or more containers, one or more pH buffers substantially free of inorganic phosphate and at least one assay component selected from the group consisting of: (a) at least one luminescent label (preferably electrochemiluminescent label); (b) at least one ECL co-reactant; (c) one or more phospho-specific binding reagents; (d) one or more electrodes and/or magnetic beads; (e) one or more blocking reagents; (f) preservatives; (g) stabilizing agents; (h) enzymes; (i) detergents; (j) desiccants and/or (k) hygroscopic agents.

Preferably, the kit comprises the assay module having one or more assay electrodes, preferably an assay plate, more preferably multi-well assay plates and the assay component (s) in one or more, preferably two or more, more preferably three or more containers according to U.S. application Ser. No. 10/185,274 (now U.S. Pat. No. 7,842,246) and Ser. No. 10/185,363 (now U.S. Pat. No. 6,977,722), each filed on Jun. 28, 2002, hereby incorporated by reference.

According to one embodiment, the kit comprises one or more of the assay components in one or more multi-well plate wells, preferably in dry form.

According to one embodiment, the assay components are in separate containers. According to another embodiment, the kit includes a container comprising binding reagents and stabilizing agents. According to another embodiment, the well reagents may include binding reagents, stabilizing agents. Preferably, the kits do not contain any liquids in the wells.

One preferred embodiment relates to a kit for use in conducting electrode induced luminescence assays (preferably electrochemiluminescence assays) comprising an assay plate, preferably a multi-well assay plate, one or more pH buffers and at least one assay component selected from the group consisting of at least one luminescent label (preferably electrochemiluminescent label) and at least one electrochemiluminescence coreactant, wherein said pH buffers comprise an ECL assay buffer background reducing agent (preferably, a non-phosphate pH buffering agent) or are substantially free of phosphate and/or said ECL coreactant is not TPA (and is preferably a functionalized tertiary alkylamine, most preferably PIPES).

Another embodiment relates to a kit comprising a multi-well plate and a pH buffer and at least one electrode induced luminescent label (preferably electrochemiluminescent label) and/or at least one bioreagent and/or at least one blocking reagent (e.g., BSA), where the kit comprises an ECL assay buffer background reducing agent (preferably, a non-phosphate buffering agent), is substantially free of inorganic phosphate and/or comprises an ECL coreactant other than TPA (preferably a functionalized tertiary alkylamine, most preferably PIPES).

According to one preferred embodiment, the kit comprises at least one material selected from group consisting of intact cell, cell lysate, cell fragment, cell membrane, membrane ghost, organelle, organelle fragment, organelle membrane, virion, virion fragment, virion membrane, liposome, detergent solubilized protein, detergent solubilized lipid or combinations thereof.

According to another embodiment, the kit comprises a biomaterial selected from the group consisting of plasma membrane fragments, endosomes, clathrin-coated vesicles, endoplamic reticulum fragments, synaptic vesicles, golgi fragments, membrane subdomains, mitochondria, peroxisomes, lysosomes, liposomes, viral particles, viral-induced membrane enclosed particles shed from cells, and intact, organismally-derived lipid membrane bodies.

According to one preferred embodiment, the kit comprises at least one bioreagent, preferably immobilized on the plate surface selected from: antibodies, fragments of antibodies, proteins, enzymes, enzyme substrates, inhibitors, cofactors, antigens, haptens, lipoproteins, liposaccharides, cells, sub-cellular components, cell receptors, viruses, nucleic acids, antigens, lipids, glycoproteins, carbohydrates, peptides, amino acids, hormones, protein-binding ligands, pharmacological agents, luminescent labels (preferably ECL labels) or combinations thereof. Preferably, at least one bioreagent is adapted or selected to binding to one or more membranes resulting in an electrode having such immobilized membranes.

Preferably, the biomaterial comprises a lipid/protein layer which contains at least one active protein selected from the group consisting of: single transmembrane receptors with intrinsic tyrosine kinase activity; non-tyrosine kinase transmembrane receptors (e.g., transferrin receptor); G-protein coupled receptors (GPCR); GPCR effector proteins (e.g., adenylate cyclase); phosphoinositides (e.g., phosphatidy inositol 4,5 bisphosphate ($PIP_2$)); phospholipid or sphingolipid composition, identification, or function (i e, changes in phosphotidylserine presence during apoptosis); organelle-bound GTPases/guanine nucleotide exchange factors (GEFs)/GTPase activating proteins (GAPs); cytokine/chemokine receptors; cell adhesion molecules (e.g., VCAM, integrins); cytoplasmic peripheral membrane protein kinases (e.g., src); intracellular protein kinase adaptor/docking proteins (e.g., insulin receptor substrate 1, GRB2); ion channels (e.g., nicotinic acetylcholine receptor, CFTR, etc.); passive transporters (e.g., glucose); active (ATP-driven) transporters; ion-linked transporters (e.g., Na+/glucose); glycosyltranferases/glycoprotein modifying enzymes; nuclear membrane fragments; and soluble receptors.

Preferably, the kit includes immobilized reagents that comprise proteins, nucleic acids, or combinations thereof.

According to one preferred embodiment, the plurality of wells includes at least two different bioreagents. For example, a well may include two or more assay domains, wherein two or more assay domains have different bioreagent Preferably, the kit comprises at least one electrochemiluminescence coreactant and/or at least one electrode induced luminescence label (preferably electrochemiluminescent label).

According to another embodiment, the kit is adapted for multiple assays. Preferably, the kit further comprises an additional assay reagent for use in an additional assay, the additional assay selected from the group consisting of radioactive assays, enzyme assays, chemical colorimetric assays, fluorescence assays, chemiluminescence assays and combinations thereof.

According to another embodiment, the kit comprises two or more, preferably four or more, more preferably eight or more, more preferably 15 or more and most preferably 25 or more assay modules or plates. According to a preferred embodiment, the kit is contained in a resealable bag or container (e.g., zip-lock opening).

Preferably, the bag or container is substantially impermeable to water. According to one preferred embodiment, the bag is a foil, preferably an aluminized foil.

The packaging may be translucent, transparent or opaque. Preferably, the plates are packaged in aluminum lined plastic containers or bags containing a dry or inert atmosphere (e.g., the bags may be sealed under an atmosphere of nitrogen or argon or the bags may contain a dessicant). According to another embodiment, the containers are vacuum sealed.

Preferably, the container contains 1 plate. According to another embodiment, the container contains ten plates. According to another embodiment, the container includes between 10 and 100 plates.

Preferably, the assay modules or plates are sterile and/or substantially free of dust and other contaminants Preferably, the assay modules are also substantially sterile.

According to one embodiment, the kit is manufactured (at least in part) and/or packaged in a “clean room” environment. Preferably, the kit is manufactured (at least in part) and/or packaged in a Class 100,000 clean room having <100,000 particles (the clean room particle count using a 0.5 micron particle count number) per cubic foot (or 3.53 million particles per cubic meter).

Preferably, the contaminant particle counts (particles less than 0.5 microns) of the kit is less than 60 million per square meter, more preferably 30 million per square meter, even more preferably less than 20 million, even more preferably less than 15 million and most preferably less than 10 million.

Preferably, the non-volatile residue in deionized water is less than 0.50 g/meter$^2$, more preferably less than 0.25 g/meter$^2$, even more preferably less than 0.15 g/meter$^2$ and most preferably less than 0.10 g/meter$^2$.

Preferably the contaminant ion concentration is less than 50 ppm, more preferably less than 20 ppm, even more preferably less than 10 ppm, even more preferably less than 5 ppm, and most preferably less than 1 ppm.

5.9 Methods

Another aspect of the present invention relates to methods of using the improved buffers, reagents and/or compositions of the invention.

One embodiment of the invention relates to a method for conducting an electrochemiluminescence assay wherein electrochemiluminescence is induced in the presence of an ECL assay buffer of the invention. Preferably, the electrochemiluminescence is induced using a carbon-based electrode.

Another embodiment of the invention relates to a method for measuring the quantity of an ECL label wherein the label is induced to emit electrochemiluminescence in the presence of an ECL assay buffer of the invention and the electrochemiluminescence is measured so as to measure the quantity of the ECL label. Preferably the electrochemiluminescence is induced using a carbon-based electrode. Most preferably, the label is bound to or held in proximity to the electrode.

Another embodiment of the invention relates to a method for measuring the quantity or activity of an analyte wherein the analyte reacts with, forms a complex with, or competes in a specific binding interaction with a labeled substance that comprises an ECL label, wherein the label is induced to emit electrochemiluminescence in the presence of an ECL assay buffer of the invention and the electrochemiluminescence is measured so as to measure the quantity or activity of the analyte. Preferably the electrochemiluminescence is induced using a carbon-based electrode. Most preferably, the presence or activity of the analyte results in the label being bound to or released from an electrode (e.g., via the formation of a specific binding complex or via a the cleavage or formation of a chemical bond).

One embodiment of the invention relates to a method for conducting an electrochemiluminescence assay wherein electrochemiluminescence is induced in the presence of a composition comprising a pH buffer and an ECL co-reactant, said composition being substantially free of inorganic phosphate and/or comprising an ECL assay buffer background reducing agent (preferably, a non-phosphate pH buffering agent).

Another embodiment of the invention relates to a method for conducting an electrochemiluminescence assay wherein electrochemiluminescence is induced in the presence of a composition comprising a pH buffer and an ECL co-reactant, wherein the ECL coreactant is a functionalized trialkylamine, preferably PIPES.

Another embodiment of the invention relates to a method of generating emission of electromagnetic radiation comprising:

(a) forming a composition comprising:
 (i) a metal-containing ECL moiety capable of being converted to an excited state from which electromagnetic radiation is emitted;
 (ii) an ECL co-reactant (preferably an amine or amine moiety) which, when oxidized, forms a strong reducing agent;
 (iii) an electrolyte capable of functioning as a medium in which said ECL moiety and said ECL co-reactant (e.g., amine or amine moiety) can be oxidized; and
 (iv) a pH buffers,
 wherein said composition is substantially free of inorganic phosphate, comprises an ECL background reducing agent (preferably, a non-phosphate pH buffering agent) and/or said ECL co-reactant is a functionalized tertiary alkylamine;
(b) exposing the composition under suitable conditions to an amount of electrochemical energy effective to induce the composition to emit electromagnetic radiation; and
(c) detecting emitted electromagnetic radiation.

Another embodiment of the invention relates to a method of effecting a specific-binding assay, either qualitatively or quantitatively, in a sample or composition comprising a pH buffer substantially free of inorganic phosphate and a phospo-specific antibody. Preferably, the sample or composition further comprises an ECL co-reactant.

Another embodiment of the invention relates to a method of effecting a specific-binding assay, either qualitatively or quantitatively, in a well having one or more assay domains with binding reagents immobilized thereon using composition comprising a pH buffer substantially free of inorganic phosphate. Preferably, the composition further comprises a phospho-specific antibody.

Another embodiment of the invention relates to a method of effecting a specific-binding non-washed assay, either qualitatively or quantitatively, in a well having one or more assay domains with binding reagents immobilized thereon using composition comprising a ECL assay buffer that is substantially free of inorganic phosphate and/or comprises an functionalized trialkylamine ECL coreactant.

Another embodiment of the invention relates to a method of performing an assay comprising forming a complex comprising a kinase product and a phospho-specific antibody, wherein said complex is not exposed to inorganic phosphate.

Another embodiment of the invention relates to a method of performing an assay comprising:

(a) forming a complex comprising a kinase product and a phospho-specific antibody, wherein said complex is not exposed to inorganic phosphate;
(b) inducing a metal-containing ECL moiety to emit electromagnetic radiation; and
(c) detecting emitted electromagnetic radiation.

Preferably, the complex further comprises said metal-containing ECL moiety.

Another embodiment of the invention relates to a method of generating emission of electromagnetic radiation, which comprises the steps of:

(a) forming a composition comprising a pH buffer, said composition being substantially free of inorganic phosphate, and (i) a metal-containing ECL moiety capable of being converted to an excited state from which electromagnetic radiation is emitted; (ii) an amine or amine moiety which, when oxidized, forms a strong reducing agent; and/or (iii) an electrolyte capable of functioning as a medium in which said ECL moiety and said amine or amine moiety can be oxidized;

(b) exposing the composition under suitable conditions to an amount of electrochemical energy effective to induce the composition to emit electromagnetic radiation; and (c) detecting emitted electromagnetic radiation.

Another aspect of the invention relates to improved assays. The invention is useful, for example, in enabling the detection and/or quantitation of one or more analytes of interest. These reactions include, for example, antigen-antibody interactions, ligand-receptor interactions, DNA and RNA interactions, enzymatic reactions, and other known reactions. In certain embodiments, the invention relates to and methods for qualitatively and quantitatively detecting the presence of analytes of interest in a multi-component sample or multi-component system. (See, U.S. application Ser. No. 10/238,391, filed on Sep. 10, 2002, now U.S. Pat. No. 7,858,321, which is hereby incorporated by reference.

One preferred aspect of the invention include methods involving one or more of the following: (a) a phospho-specific antibody; (b) assay involving capture reagents immobilized on a solid surface comprising an electrode or adjacent an electrode; and/or (c) assays involving low detection levels (and/or requiring high signal to background ratio).

The embodiments of the invention can be used to test a variety of samples which may contain an analyte or activity of interest. Such samples may be in solid, emulsion, suspension, liquid, or gas form. They may be, but are not limited to, samples containing or derived from, for example, cells (live or dead) and cell-derived products, immortalized cells, cell fragments, cell fractions, cell lysates, organelles, cell membranes, hybridoma, cell culture supernatants (including supernatants from antibody producing organisms such as hybridomas), waste or drinking water, food, beverages, pharmaceutical compositions, blood, serum, plasma, hair, sweat, urine, feces, tissue, biopsies, effluent, separated and/or fractionated samples, separated and/or fractionated liquids, organs, saliva, animal parts, animal byproducts, plants, plant parts, plant byproducts, soil, minerals, mineral deposits, water, water supply, water sources, filtered residue from fluids (gas and liquid), swipes, absorbent materials, gels, cytoskeleton, protein complexes, unfractionated samples, unfractionated cell lysates, endocrine factors, paracrine factors, autocrine factors, cytokines, hormones, cell signaling factors and or components, second messenger signaling factors and/or components, cell nucleus/nuclei, nuclear fractions, chemicals, chemical solutions, structural biological components, skeletal (ligaments, tendons) components, separated and/or fractionated skeletal components, hair, fur, feathers, hair fractions and/or separations, skin, skin samples, skin fractions, dermis, endodermis, eukaryotic cells, prokaryotic cells, fungus, yeast, antibodies, antibody fragments, immunological factors, immunological cells, drugs, therapeutic drugs, oils, extracts, mucous, fur, oils, sewage, environmental samples, organic solvents or air. The sample may further comprise, for example, water, organic solvents (e.g., acetonitrile, dimethyl sulfoxide, dimethyl formamide, n-methyl-pyrrolidone or alcohols) or mixtures thereof.

Analytes that may be measured include, but are not limited to, whole cells, cell surface antigens, subcellular particles (e.g., organelles or membrane fragments), viruses, prions, dust mites or fragments thereof, viroids, antibodies, antigens, haptens, fatty acids, nucleic acids (and synthetic analogs), proteins (and synthetic analogs), lipoproteins, polysaccharides, inhibitors, cofactors, haptens, cell receptors, receptor ligands, lipopolysaccharides, glycoproteins, peptides, polypeptides, enzymes, enzyme substrates, enzyme products, second messengers, cellular metabolites, hormones, pharmacological agents, synthetic organic molecules, organometallic molecules, tranquilizers, barbiturates, alkaloids, steroids, vitamins, amino acids, sugars, lectins, recombinant or derived proteins, biotin, avidin, streptavidin, or inorganic molecules present in the sample. Activities that may be measured include, but are not limited to, the activities of phosphorylases, phosphatases, esterases, trans-glutaminases, nucleic acid damaging activities, transferases, oxidases, reductases, dehydrogenases, glycosidases, ribosomes, protein processing enzymes (e.g., proteases, kinases, protein phophatases, ubiquitin-protein ligases, etc.), nucleic acid processing enzymes (e.g., polymerases, nucleases, integrases, ligases, helicases, telomerases, etc.), cellular receptor activation, second messenger system activation, etc.

Whole cells may be animal, plant, or bacteria, and may be viable or dead. Examples include plant pathogens such as fungi and nematodes. The term "subcellular particles" is meant to encompass, for example, subcellular organelles, membrane particles as from disrupted cells, fragments of cell walls, ribosomes, multi-enzyme complexes, and other particles which can be derived from living organisms. Nucleic acids include, for example, chromosomal DNA, plasmid NA, viral DNA, and recombinant DNA derived from multiple sources. Nucleic acids also include RNA's, for example messenger RNA's, ribosomal RNA's and transfer RNA's. Polypeptides include, for example, enzymes, transport proteins, receptor proteins, and structural proteins such as viral coat proteins. Preferred polypeptides are enzymes and antibodies. Particularly preferred polypeptides are monoclonal antibodies. Hormones include, for example, insulin and T4 thyroid hormone. Pharmacological agents include, for example, cardiac glycosides. It is of course within the scope of this invention to include synthetic substances which chemically resemble biological materials, such as synthetic polypeptides, synthetic nucleic acids, and synthetic membranes, vesicles and liposomes. The foregoing is not intended to be a comprehensive list of the biological substances suitable for use in this invention, but is meant only to illustrate the wide scope of the invention.

The composition or reagent of the invention are preferably aqueous. The composition or reagent can also be non-aqueous. Examples of suitable organic liquids are acetonitrile, dimethylsulfoxide (DMSO), dimethylformamide (DMF), methanol, ethanol, and mixtures of two or more of the foregoing. Illustratively, tetraalkylammonium salts, such as tetrabutylammonium tetrafluoroborate, are soluble in organic liquids and can be used with them to form non-aqueous electrolytes.

Also, typically, the analyte of interest is present at a concentration of $10^{-3}$ molar or less, for example, at least as low as $10^{-18}$ molar. The sample which may contain the analyte of interest, can be in solid, emulsion, suspension, liquid, or gas form, and can be derived from, for example, cells and cell-derived products, water, food, blood, serum, hair, sweat, urine, feces, tissue, saliva, oils, organic solvents or air. The sample can further comprise, for example, water, acetonitrile, dimethyl sulfoxide, dimethyl formamide, n-methyl-pyrrolidone or alcohols.

In one embodiment, the reagent includes an ECL moiety conjugated to an antibody, antigen, nucleic acid, hapten, small nucleotide sequence, oligomer, ligand, enzyme, or biotin, avidin, streptavidin, Protein A, Protein G, or complexes thereof, or other secondary binding partner capable of binding to a primary binding partner through protein interactions.

One embodiment of the invention relates to a method of detecting or quantitating an analyte of interest by ECL assay, which comprises:

(1) forming a composition comprising (a) a sample to be tested for the analyte of interest, (b) at least one substance selected from the group consisting of (i) additional analyte of interest or an analog of the analyte of interest, (ii) a binding partner of the analyte of interest or its said analog, and (iii) a reactive component capable of binding with (i) or (ii), (c) a metal-containing ECL moiety capable of being converted to an excited state from which electromagnetic radiation is emitted, said ECL moiety being capable of entering into a binding interaction with the analyte of interest or a substance defined in (b)(i), (b)(ii), or (b)(iii);

(d) an ECL co-reactants (preferably an amine or an amine moiety) which, when oxidized, forms a strong reducing agent, and (e) an electrolyte capable of functioning as a medium in which said ECL moiety and said species can be oxidized;

(2) exposing said composition to an amount of electrochemical energy effective to induce the composition to emit electromagnetic radiation; and (3) detecting emitted electromagnetic radiation, wherein the sample is not exposed to inorganic phosphate detrimental to the performance of the assay or wherein said composition further comprises an ECL assay buffer background reducing agent (preferably, a non-phosphate pH buffering agent). Preferably, the composition has less than 15 mM inorganic phosphate, more preferably it has less than 5 mM inorganic phosphate, even more preferably it has less than 1 mM phosphate, even more preferably it is substantially free of inorganic phosphate, most preferably it is free of inorganic phosphate.

Solid phase assay formats (e.g., solid phase binding assays) often couple a biological activity or binding reaction to attachment or dissociation of a label from a surface. For example the binding interaction between a binding reagent that is attached and a labeled analyte results in the localization of the label on the solid phase supporting the immobilized binding reagent. The biological activity or binding reaction to be measured can be quantified through a measurement of the labels on the solid phase. Many solid phase assay formats involve a wash step to remove unbound labels prior to detecting labels on the solid phase (washed assays). Assays without this wash step can be achieved when the detection method can discriminate between free and bound labels. Non-wash assay formats are desired because washing steps, in many applications, can be difficult or cumbersome to carry out. In many cases, however, the performance of non-wash assays is limited by high background signals due to incomplete discrimination of free vs. bound labels.

We have found, surprisingly, that the ECL assay buffers of the invention improve the discrimination of free vs. bound labels in ECL assays using assay reagents attached (e.g., by covalent interactions, specific binding interaction, non-specific adsorption, etc,) to the working electrode used to induce ECL (i.e., the ability to selectively detect labels that are bound to the electrode). More specifically, the compositions and reagents of the invention improve the ratio of ECL signal from bound label to ECL signal from free label. It is believed that the ECL assay buffers of the invention decrease the distance from the solid electrode surface from which an ECL label is induced to emit luminescence. This, in turn, increases the signal of bound label (which may be bound to the electrode surface) vs. free label (which is not bound to the electrode). Another way to characterize this is in terms of an "effective excitation length"—the maximum distance at which a free ECL label is able to be excited. The "effective excitation length" is impacted by i) the distance short-lived intermediates involved in the generation of ECL (e.g., oxidation product of TPA) can diffuse from the electrode before they are destroyed in a destructive side reaction (a function of the lifetimes and diffusion constants for these intermediates) and ii) the rate at which free labels or labeled reagents diffuse into the region close enough to the electrode to participate in a reaction with these reactive intermediates (a function of the diffusion constant for the unbound ECL labels or labeled reagents).

Using the ECL assay buffers of the invention, the effective excitation length is reduced by >50%, preferably by >75%, even more preferably by >90%. Thus, the ECL assay buffers of the invention are desirable since they maximize the ratio of bound/free ECL signal which enhances the performance of the assay. These considerations are particularly important for measuring low affinity interactions, which require the presence of the labeled species in high concentration in the solution but would also be expected to suffer from significant signal loss due to binding complex dissociation during wash steps.

Accordingly, another aspect of the invention relates to non-wash format assays using pH buffer substantially free of inorganic phosphate which maximizes the ratio of bound/free ECL signal. Preferably, the assay involves the capture of an ECL label at a surface having or being adjacent to an electrode surface. See, for example, U.S. Pat. Nos. 6,066,448; 6,090,545; 6,140,045; 6,207,369, 6,214,369; and U.S. application Ser. No. 10/185,274 (now U.S. Pat. No. 7,842,246) and Ser. No. 10/185,363 (now U.S. Pat. No. 6,977,722), each filed on Jun. 28, 2002, hereby incorporated by reference.

Thus, another embodiment of the invention relates generally to electrochemiluminescence assays using reagents immobilized on a surface (preferably an electrode surface) and having advantageous effective excitation lengths. Preferably, the assay results in an effective excitation length less then 100 microns, more preferably less than 75 microns, even more preferably less than 50 microns, even more preferably less than 25 microns, even more preferably less than 10 microns, even more preferably less than 5 microns and most preferably less than 1 micron. According to a particularly preferred, embodiment, the effective excitation length is less than 0.5 micron, preferably less than 0.2 microns, even more preferably less than 0.1 micron.

5.10 Systems

Yet another aspect of the present invention relates to system for performing assays and comprising or using the reagents and/or compositions of the invention.

One embodiment of the invention relates to a system for ECL detection or quantitation of an analyte of interest in a sample, said system comprising:

(a) a pH buffering agent;

(b) a sample;

(c) at least one substance selected from the group consisting of:

(i) added analyte of interest or an analog of the analyte of interest, (ii) a binding partner of the analyte of interest or its said analog, and (iii) a reactive component capable of binding with (i) or (ii), wherein one of said substances is linked, either directly or through one or more other molecules, to a metal-containing ECL moiety which is capable of being converted to an excited state from which electromagnetic radiation is emitted;

(d) an ECL co-reactant, preferably an amine or amine moiety, which is capable of being converted to a strong reducing agent and an electrolyte;

(d) one or more electrodes for inducing the ECL moiety to emit electromagnetic radiation; and (e) one or more detectors for measuring the emitted radiation to determine the presence or quantity of the analyte of interest in the sample;

Wherein said pH buffering agent is substantially free of phosphate or is an ECL assay buffer background reducing agent and/or said ECL coreactant is a functionalized tertiary amine.

Another embodiment of the invention relates to a system for ECL detection or quantitation of an analyte of interest in a sample, said system comprising:

(a) a pH buffering agent;

(b) a sample;

(c) at least one substance selected from the group consisting of:

(i) added analyte of interest or an analog of the analyte of interest, (ii) a binding partner of the analyte of interest or its said analog, and (iii) a reactive component capable of binding with (i) or (ii), wherein one of said substances is linked, either directly or through one or more other molecules, to a metal-containing ECL moiety which is capable of being converted to an excited state from which electromagnetic radiation is emitted;

(d) an ECL co-reactant, preferably a functionalized tertiary amine, which is capable of being converted to a strong reducing agent and an electrolyte;

(d) one or more electrodes for inducing the ECL moiety to emit electromagnetic radiation; and (e) one or more detectors for measuring the emitted radiation to determine the presence or quantity of the analyte of interest in the sample.

5.11 Method of Selecting Biologically Active Compounds and Producing Novel Drugs Another aspect of the invention relates to improved methods and systems for selecting or identifying biologically active compounds and, optionally, incorporating such biologically active compounds into suitable carrier compositions in appropriate dosages as described in paragraph 6.11 of U.S. application Ser. No. 10/185,274 (now U.S. Pat. No. 7,842,246) and Ser. No. 10/185,363 (now U.S. Pat. No. 6,977,722), each filed on Jun. 28, 2002, hereby incorporated by reference.

One embodiment relates to the use of the invention to screen for new drugs, preferably, by high-throughput screening (HTS), preferably involving screening of greater than 50, more preferably 100, more preferably 500, even more preferably 1,000, and most preferably 5,000. According to a particularly preferred embodiment, the screening involves greater than 10,000, greater than 50,000, greater than 100, 00, greater than 500,000 and/or greater than 1,000,000 compounds.

Advantageously, the reagents, compositions, methods, apparatus and/or assay plates or modules of the invention may be integrated into and/or used in a variety of screening and/or drug discovery methods. Such screening and/or drug discovery methods include those set forth in U.S. Pat. No. 5,565,325 to Blake; U.S. Pat. No. 5,593,135 to Chen et al.; U.S. Pat. No. 5,521,135 to Thastrup et al.; U.S. Pat. No. 5,684,711 to Agrafiotis et al.; U.S. Pat. No. 5,639,603 to Dower et al.; U.S. Pat. No. 5,569,588 to Ashby et al.; U.S. Pat. No. 5,541,061; U.S. Pat. No. 5,574,656; and U.S. Pat. No. 5,783,431 to Peterson et al.

According to another embodiment, the invention further comprises identifying adverse effects associated with the drug and storing information relating to the adverse effects in a database. See, U.S. Pat. No. 6,219,674 by Classen.

Another aspect of the invention relates to improved biologically active compounds and/or drugs made using the inventive methods.

6. EXAMPLES

The following examples are illustrative of some of the electrodes, plates, kits and methods falling within the scope of the present invention. They are, of course, not to be considered in any way limitative of the invention. Numerous changes and modification can be made with respect to the invention by one of ordinary skill in the art without undue experimentation.

Example I

ECL Measurements

Unless otherwise indicated, ECL measurements were carried out using multi-well plates having integrated carbon ink electrodes (see, Example 6.1 and, in particular, Plate Types A and B of U.S. application Ser. No. 10/185,274 (now U.S. Pat. No. 7,842,246) and Ser. No. 10/185,363 (now U.S. Pat. No. 6,977,722), each filed on Jun. 28, 2002, hereby incorporated by reference). The electrodes were, optionally treated with an oxygen plasma prior to being coated with binding reagents (plasma treated and non-plasma treated plates, respectively, are designated hereafter as PT or NPT plates). Binding reagents were immobilized on the working electrodes of the plates using the methods described in the U.S. application Ser. No. 10/185,274 (now U.S. Pat. No. 7,842,246) and Ser. No. 10/185,363 (now U.S. Pat. No. 6,977,722), or adaptations thereof. Unless otherwise indicated, ECL measurements were carried out using multi-well plate readers adapted for use with these multi-well plates. The readers and their use are described in Example 6.3 of the U.S. application Ser. No. 10/185,274 and Ser. No. 10/185,363. U.S. application Ser. No. 10/185,274 (now U.S. Pat. No. 7,842,246) and Ser. No. 10/185,363 (now U.S. Pat. No. 6,977,722). These applications and, in particular, the descriptions of plate types, immobilization methods, plate readers and ECL measurement methods disclosed therein, are hereby incorporated by reference. The reported ECL intensities are reported in relative terms and may depend on the instrument, gain settings and plates used in a particular experiment. For this reason, the absolute values reported in different experiments may not be directly comparable.

Example II

Tyrosine Kinase Assay

The format involved the phosphorylation of a kinase substrate immobilized on electrodes in multi-well plates adapted for ECL measurements (see Example I), complexation of the product to a labeled anti-phosphotyrosine antibody and detection of the surface-bound label via an ECL measurement in the presence of an ECL Assay Buffer comprising an ECL coreactant. The electrodes were pretreated by etching in an oxygen plasma to increase the amount of exposed carbon. The kinase substrate—poly(Glu, Tyr) having a 4:1 ratio of Glu to Tyr and a molecular weight of 20,000-50,000 Daltons (PGT, Sigma-Aldrich Co.)—was immobilized by non-specific adsorption on the surface of the working electrodes in the wells of the plates. The working electrode in each well was treated with 1500 nL of a solution containing 1 mg/ml PGT in PBS buffer. The plate was then dried overnight and blocked in a 5% solution of bovine serum albumin at 4° C. The plate was washed to remove the blocking agent prior to use.

The assay was carried out by adding, to each well, 50 μL of a buffered solution containing a soluble tyrosine kinase (c-src, Upstate Biotechnology), an anti-phosphotyrosine monoclonal antibody (Abzyme, IGEN International) that was labeled with a sulfonated derivative of ruthenium-tris-bipyridine (Sulfo-TAG™ label, Meso Scale Discovery), ATP and $Mg^{+2}$. The reaction was allowed to proceed for 1 hour. The plate was washed and 100 μL of an ECL Assay Buffer containing tripropylamine was added. The plate was analyzed using electrochemiluminescence detection as described in Example I.

When a conventional ECL Assay Buffer containing TPA in a phosphate buffer (ORIGEN Assay Buffer, IGEN International) was used in the protocol, the complex formed between the labeled antibody and the phosphorylated substrate dissociated over a period of 30 min. to an hour (the majority of the dissociation occurring within the first few minutes) due to the competitive binding of phosphate ions with the labeled antibodies. One approach to avoiding this problem is to control the time of exposure of the formed complex to the inorganic phosphate-containing solution. This approach, however, may be impractical in some assays such as high throughput assays involving large numbers of plates.

Applicants discovered another solution to overcome the problem was the use of phosphate-free buffers. Surprisingly, it was discovered that the phosphate could be replaced with other buffers without compromising the ability of the ECL Assay Buffers to support the generation of ECL.

Assays were carried out using the following two ECL Assay Buffer compositions:

Gly-Gly Assay Buffer:
0.4 M Glycylglycine (Gly-Gly)
0.1 M Tripropylamine (TPA)
12 mM Ethylenediaminetetraacetic Acid (EDTA)
pH=7.8 (adjusted by addition of 10% KOH)

Tris Assay Buffer:
0.4 M Tris(hydroxymethyl)aminomethane (Tris)
0.15 M Tripropylamine (TPA)
12 mM Ethylenediaminetetraacetic Acid (EDTA)
pH=7.8 (adjusted by addition of 10% KOH)

EDTA was added into the new ECL Assay Buffers to stop the phosphorylation reaction by sequestering $Mg^{+2}$, an ion required for kinase activity (EDTA was not required in phosphate-based ECL Assay Buffers due to the affinity of phosphate for magnesium ions). This composition allowed us to combine two steps (addition of stop-solution and actual assay buffer) into one step. Applicants found that EDTA interfered with ECL generation at concentrations higher that 10 mM, but that 5-12 mM EDTA was enough to stop the reaction while only causing a small decrease in ECL signal.

Figure 1:
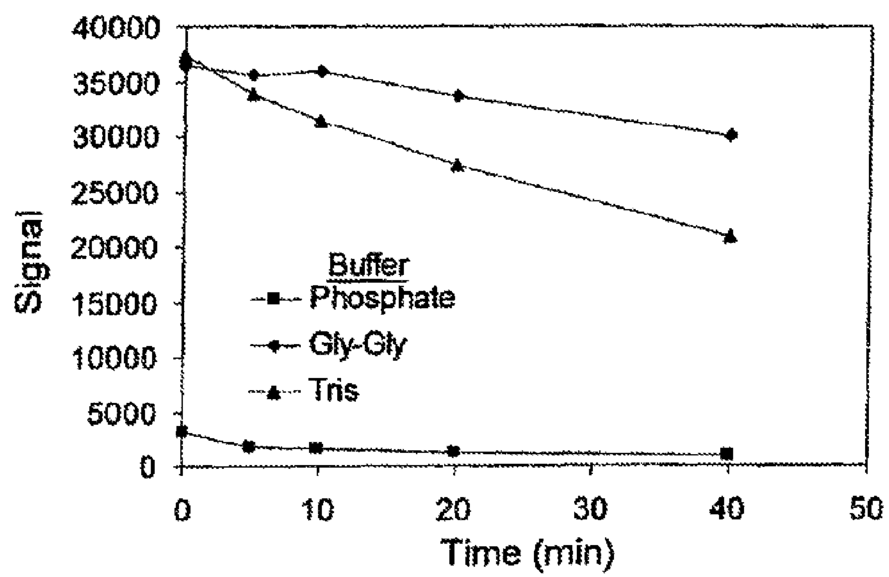

FIG. 1 shows the decrease in ECL from the phosphopeptide-antibody complex as a function of the time between the addition of the Assay Buffer and the measurement of ECL. Surprisingly, while exposure of the complex to the phosphate-containing ORIGEN Assay Buffer led to almost complete dissociation of the complex (within the time it took to put the plate into the ECL reader for the 0 min. point), the complex showed excellent stability in the Gly-Gly (<80% dissociation over 40 min) and Tris (<55% dissociation over 40 min) Assay Buffers.

Figure 2:
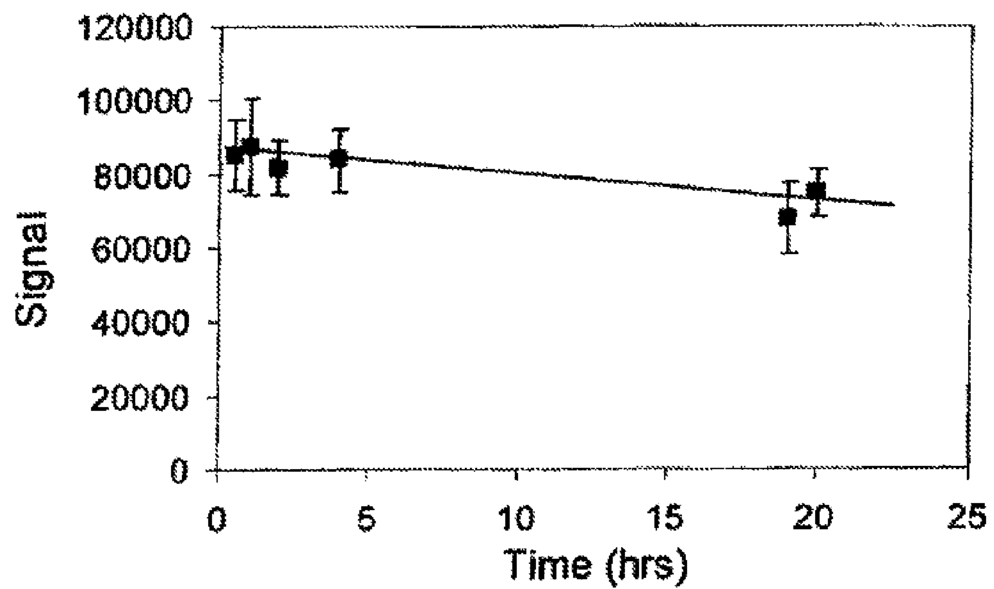
FIG. 2 shows the rate of dissociation of a phosphopeptide-antiphosphopeptide complex in an ECL Assay Buffer that comprises TPA as an ECL coreactant and Tris as a pH buffering agent. The complex was not washed to remove free antibody prior to addition of the ECL Assay Buffer.

The stability of the complex was improved further by eliminating the wash step prior to addition of the assay buffer. FIG. 2 shows the results of an experiment in which 200 μL of Gly-Gly Assay Buffer (as described above except that the concentration of EDTA was 5 mM and 0.2% Triton X-100 was added) was added directly to the reaction mixture without an intervening wash step. Storage of the plates for 20 hours prior to measuring ECL resulted in only a 15% decrease in signal.

One additional surprising advantage of the protocol was its robustness. Surprisingly, the time of the phosphorylation step was the only time that required tight control in order to get reproducible results. The results of the assay did not depend on the time between all other steps.

Example III

Detection of Phosphorylated EGF Receptor

A sandwich immunoassay was used to detect autophosphorylated α-epidermal growth factor receptor (α-EGFR) in cell lysates prepared from EGF-activated A-431 cells (American Type Culture Collection). The assay employed a biotin labeled capture antibody directed against the α-EGFR extracellular domain and a Sulfo-TAG labeled detection antibody that is specific for phosphotyrosine (see Example II). The biotin-labeled antibody was immobilized on the working electrode of multi-well plates adapted for use in ECL assays (see Example I) through the interaction of the biotin label with avidin that was passively adsorbed on the electrode surface. Solubilized EGFR (in RIPA, a deoxycholate-containing buffer) was then added and allowed to bind to the anti-EGFR antibody. Subsequently, the Sulfo-TAG labeled α-phosphotyrosine antibody was added to detect autophosphorylated EGFR.

Figure 3:
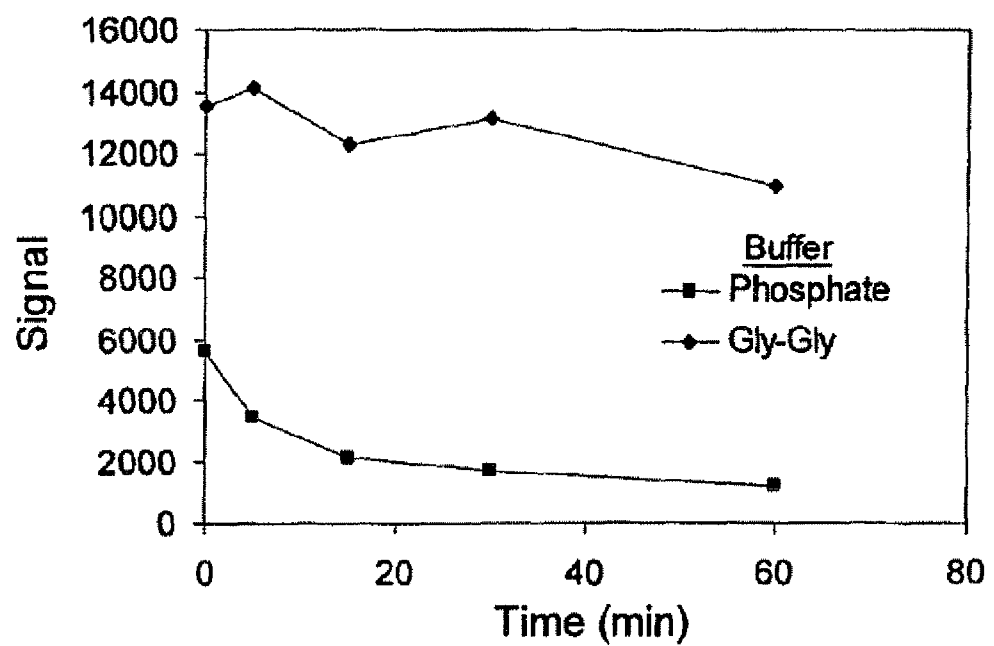
FIG. 3 is a graphical representation of an end-product stability study comparing the dissociation rate of an anti-phosphotyrosine antibody from autophosphorylated EGF receptor in two different ECL Assay Buffers: 150 mM TPA/150 mM Phosphate and 100 mM TPA/400 mM glycylglycine. The concentration of the labeled α-phosphotyrosine antibody was 6.7 nM.

In an end-product stability experiment, an assay was carried out as described above and, prior to the induction and measurement of ECL, the resulting sandwich complex was incubated for varying amounts of time in two different ECL Assay Buffers: 150 mM TPA/150 mM Phosphate, pH 7.48 and 100 mM TPA/400 mM glycine-glycine, pH 7.8. FIG. 3 shows that there was a significant time-dependent decay in signal in the presence of the phosphate-containing buffer; the signal decreased by roughly 80% after one hour. The glycine-glycine buffer reduced this decrease to roughly 20%. The great loss of signal that occurs in the phosphate buffer is believed to be due to the phosphate ion competing with the phosphorylated protein for the anti-phosphotyrosine antibody. Moreover, the signal to background ratio was increased 2.5 fold using the glycyl-glycine assay buffer.

Example IV

Effect of ECL Assay Buffer Composition on the Ability to Discriminate Between Specific Signal and Assay Buffer Background In many ECL assay formats, the sensitivity with which an ECL label can be measured is limited by the light signal (and the noise in the light signal) generated by the ECL Assay Buffer in the absence of the ECL label (ECL Assay Buffer background). This limitation is especially evident in washed assays, assays exhibiting low levels of non-specific binding and/or assays employing ECL readers having sensitive, low noise, light detectors. Applicants examined the relationship between ECL Assay Buffer composition and the ability to discriminate between the signal due to an ECL label and the ECL Assay Buffer background. In particular, applicants tested four ECL Assay Buffer formulations that varied in the identity of the ECL coreactant and/or the identity of the pH buffering agent: TPA/Phosphate, TPA/Tris, TPA/Gly-Gly and PIPES/Phosphate (where PIPES stands for 1,4-piperazine-1,4-bis(2-ethanesulfonic acid).

The experiments were carried out on multi-well plates (as described in Example I) that had avidin immobilized on the working electrodes. The experiments were carried out on plates that were treated with an oxygen plasma (PT plates) as well as on untreated plates (NPT plates). Avidin was immobilized on PT plates by dispensing 2.5 uL of solution containing 0.5 mg/mL avidin and 0.0035% Triton X-100 on the working electrode of each well, allowing the solution to evaporate to dryness over a period of 1 hour and blocking the remaining surfaces of the well overnight at 4° C. with a 5% (w/v) solution of BSA. Avidin was immobilized on NPT plates by dispensing 2.5 uL of solution containing 0.5 mg/mL avidin and 0.0075% Triton X-100 on the working electrode of each well, allowing the solution to evaporate to dryness overnight and blocking the remaining surfaces of the well for 2 hours with a 5% (w/v) solution of BSA. Varying amounts of an ECL label could be brought into proximity with the electrode surface by treating the wells with a solution containing bovine IgG that was labeled with biotin and ~1.9 Sulfo-TAG labels per protein (BT-IgG*). The binding of the BT-IgG* was accomplished by adding 50 uL of a solution containing 1 nM of BT-IgG* in PBS to the wells and incubating for a period of 60 minutes while shaking. The wells were washed with water, 100 uL of ECL Assay Buffer was added and ECL was measured. The signal due to ECL Assay Buffer Background was measured by repeating the experiment as described above except that the BT-IgG* was omitted.

The four combinations of coreactant and pH buffer to be tested were optimized to identify the concentration of coreactant, the concentration of pH buffer and the pH that gave the best ratio of signal from BT-IgG* to ECL Assay Buffer background (S/B ratio). The concentrations of coreactant were varied from 25 to 200 mM for TPA or 13 to 200 mM for PIPES. The concentrations of pH buffer were varied from 50 to 300 mM for phosphate, 100-600 mM for Tris or 50-800 mM for Gly-Gly. The pH was varied from 7 to 8. In all cases, the ECL Assay Buffers also contained 0.05% Triton X-100. KOH or HCl were added as necessary to achieve the desired pH. Within the ranges tested, all the formulations gave adequate performance for use in ECL assays, however, the following optimized formulations were identified on the basis of their S/B ratios: TPA/Phosphate (125 mM TPA, 200 mM phosphate, 0.05% Triton X-100, pH 7.5); TPA/Tris (125 mM TPA, 200 mM Tris, 0.05% Triton X-100, pH 7.8); TPA/Gly-Gly (100 mM TPA, 200 mM Gly-Gly, 0.05% Triton X-100, pH 7.8) and PIPES/Phos (25 mM PIPES, 100 mM phosphate, 0.05% Triton X-100, pH 7.5).

FIGS. 4A and 4B compare the performance of the four optimized formulations for assays carried out on NPT plates and PT plates, respectively. We found that the TPA/Phosphate and TPA/Tris buffers gave roughly comparable signals for the BT-IgG*, however, the lower ECL Assay Buffer Background of the TPA/Tris system led to a significant improvement in the S/B ratio relative to the TPA/Phosphate buffer. Assuming the noise in the background to be roughly proportional to the background signal, the 4-6 fold improvement in S/B ratio transfers directly to a 4-6 fold improvement in detection limits. Despite having lower specific signals, the TPA/Gly-Gly buffer had an S/B ratio that was approximately the same as the TPA/Tris buffer and could, therefore, be expected to produce similar detection limits. The PIPES/Phosphate buffer performed slightly better (in terms of S/B ratio) than the TPA/Phosphate buffer on unetched plates and slightly worse on etched plates.

Example V

Effect of the ECL Assay Buffer Composition on the Ability to Discriminate Between ECL Labels that are Bound to an Electrode Surface and ECL Labels that are Free in Solution In some ECL assay formats, the sensitivity with which an ECL label held in proximity to an electrode can be measured is limited by the light signal (and the noise in the light signal) generated by ECL labels in solution. This limitation is especially evident in assays in which labels in solution are not removed by washing prior to the addition of an ECL Assay Buffer and the measurement of ECL (Unwashed Assays). Applicants examined the relationship between ECL Assay Buffer composition and the ability to discriminate between the signal due to ECL labels bound to (or held in proximity to) an electrode and ECL labels that are free in solution.

In these experiments, the specific signal from bound ECL labels was measured using BT-IgG* bound to avidin-coated electrodes as described in Example IV. The ECL Assay Buffer background was determined by omitting the BT-IgG*, also as described in Example IV. The ECL signal from free ECL labels in solution was determined similarly to the ECL Assay Buffer background except that the ECL Assay Buffer added to the wells included 10 nM bovine IgG having 3.9 labels per protein (IgG*). The ratio of the ECL signal from the bound BT-IgG* to the ECL signal from the free IgG* (B/F ratio) is indicative of the sensitivity with which bound ECL labels can be detected in the presence of free ECL labels in solution.

The four optimized ECL Assay Buffers from Example IV were tested for their ability to discriminate between surface bound ECL labels. The results are presented in Tables IA and IB. The replacement of phosphate with Tris led to some improvement in the B/F ratio for TPA-containing buffers. The most drastic improvement, however, was achieved by substituting the coreactant component, i.e., by replacing TPA with PIPES. There was a 4-5 fold improvement in the B/F ratio by replacing TPA/Phos with PIPES/Phos.

TABLE IA

ECL signal measured on avidin-coated PT plates from bound BT-IgG* (bound from a 1.5 nM solution), free IgG* (present in a 1.5 nM solution) and ECL Assay Buffer Background.

| | Bound BT-IgG* | Free IgG* | Background | S/B | B/F |
|---|---|---|---|---|---|
| TPA/Phosphate | 77493 | 2267 | 305 | 254 | 39 |
| TPA/Tris | 83167 | 1873 | 61 | 1363 | 46 |
| TPA/Gly-Gly | 28168 | 1111 | 35 | 805 | 26 |
| PIPES/Phosphate | 64724 | 670 | 319 | 203 | 183 |

S/B = (Bound)/(Background);
B/F = (Bound-Background)/(Free-Background).

TABLE IB

ECL signal measured on avidin-coated NPT plates from bound BT-IgG* (bound from a 1.5 nM solution), free IgG* (present in a 1.5 nM solution) and ECL Assay Buffer Background.

| | Bound BT-IgG* | Free IgG* | Background | S/B | B/F |
|---|---|---|---|---|---|
| TPA/Phosphate | 264,063 | 4671 | 464 | 569 | 63 |
| TPA/Tris | 270,809 | 2734 | 89 | 3043 | 102 |
| TPA/Gly-Gly | 123,393 | 1663 | 38 | 3247 | 76 |
| PIPES/Phosphate | 172,226 | 728 | 164 | 1050 | 305 |

S/B = (Bound)/(Background);
B/F = (Bound-Background)/(Free-Background).

PIPES-containing ECL Assay Buffers were prepared with phosphate, Tris or Gly-Gly as the buffering agent. The B/F ratio of each of these mixtures was further optimized by varying the concentration of PIPES and the buffer component. The concentration of PIPES was varied from 12.5 to 200 mM in the phosphate-based buffer and 25 to 100 mM in the Tris and Gly-Gly buffers. The concentrations of the buffering agent were varied from 100 to 400 mM. In all cases, the ECL Assay Buffers also contained 0.05% Triton X-100. KOH or HCl were added as necessary to achieve the desired pH. Within the ranges tested, all the formulations gave adequate performance for use in ECL assays including compositions that had no added buffer component. It was also possible to omit the buffering agent and achieve adequate performance due the ability of PIPES to act as a pH buffer. PIPES concentrations of 20-100 mM were found to provide high B/F ratios while maintaining reasonable ECL intensities. The best performance was achieved when the phosphate concentrations was roughly 2-4 times the PIPES concentration. The following optimized formulations were identified on the basis of having both high S/B ratios and reasonable signal intensities: PIPES/PHOSPHATE (25 mM PIPES, 100 mM phosphate, 0.05% Triton X-100, pH 7.5); PIPES/Tris (25 mM PIPES, 200 mM Tris, 0.05% Triton X-100, pH 7.8) and PIPES/Gly-Gly (25 mM PIPES, 100 mM Gly-Gly, 0.05% Triton X-100, pH 7.8).

FIGS. 5A and 5B compare the performance of the three optimized formulations for nonwashed assays carried out on NPT plates and PT plates, respectively. The figures compare the performance to the conventional TPA/Phosphate buffer. We found that for all three buffering agents that were tested, the use of PIPES as a coreactant led to significant improvements (as much as factors of 4-5) in the B/F ratio relative to TPA/Phosphate.

Example VI

Effect of Detergent on the Performance of ECL Assay Buffers

FIG. 6 shows the effect of the presence of various non-ionic detergents on ECL signal from BT-IgG* bound to avidin-coated plasma treated electrodes. The detergents were added at 0.5%(w/v) to one of two ECL Assay Buffers: FIG. 6A shows the results obtained with 150 mM TPA, 250 mM phosphate, pH 7.5; FIG. 6B shows the results obtained with 50 mM PIPES, 150 mM phosphate, pH 7.5. BT-IgG* (50 μL of a 0.01 nM solution) was allowed to bind to the avidin surface. The plates were washed, ECL Assay Buffers were added and the plates were analyzed using ECL detection. The figure shows the Assay Buffer background, signal and S/B ratio (calculated as in Example 4) measured using each of the ECL Assay Buffers. Of the detergents tested, only Triton X-100 had a significant effect on performance. For the PIPES-based buffer, the effect was large; addition of Triton led to a >2.5 fold increase in the S/B ratio. The effect of Triton X-100 on the TPA-based buffer was much smaller. Triton X-100 differs from the other detergents present in that it contains a phenol ether moiety. Applicants hypothesize that the beneficial effect of Triton X-100 may result from the oxidation of the phenol ether moiety at the electrode and the participation of the Triton oxidation product in the ECL reaction.

Surprisingly, the effect of detergents on assays conducted on non-plasma treated plates was different and much greater in magnitude. FIG. 7 shows the effect of five different non-ionic detergents on TPA/Phos, TPA/Tris, TPA/Gly-Gly and PIPES/Phos Assay Buffers (the optimized formulations of Example IV except for the composition and amount of detergent). Tween 20, Thesit, Triton X-100 and Triton X-114 were all present at a concentration of 0.05%(v/v). β-Octyl glucopyranoside was present at a concentration of 4%(v/v). In this experiment, streptavidin-coated electrodes were treated with 0.018 pmol of BT-IgG* (6.3 labels per protein) in a volume of 50 uL. The figure shows that all the detergents significantly improved the ECL signal measured in the presence of TPA-containing Assay Buffers relative to the same Assay Buffer in the absence of detergent. In most cases, the improvement was greater than 2 fold. In additional experiments, it was observed that the maximal signals observed in each Assay Buffer tended to occur at the critical micellar concentration (cmc) of a detergent or higher. In contrast to the TPA-containing ECL Assay Buffers, the performance of PIPES was improved ~30 fold by the addition of the phenol ether containing detergents (Triton X-100 and Triton X-114) but very little improvement in signal was observed in the presence of the Tween and Thesit detergents.

Applicants hypothesize that the effect of the Triton detergents on the PIPES/Phos buffer may be related to the participation of Triton oxidation products in the ECL process. By contrast, the effect of detergents on the ECL signal from TPA-containing Assay Buffers on NPT electrodes appears to be a more general phenomenon and may relate to the stabilization of TPA oxidation products in detergent micelles.

A larger screen of detergents was conducted to identify other detergents that improved the ECL signal from BT-IgG* on streptavidin-coated NPT electrodes in the presence of TPA/Phosphate. The addition of all the non-ionic detergents (APO-14, Triton X-100, β-nonyl-glucoside, Tween 20, Genapol and pentaethylene glycol mono-n-dodecyl ether) and zwitterionic detergents (ASB-14 and Empigen) that were tested produced increases in the ECL signal.

Example VII

ECL Activity of Selected Tertiary Amines

A number of tertiary amines were screened for their ability act as coreactants. The measurements were conducted in a similar fashion as the methods described in Examples IV and V. ECL Assay Buffers were prepared that contained the selected tertiary amine (200 mM), phosphate buffer (200 mM), Triton X-100 (0.1%) and that were adjusted to pH 7.5. The signal from label attached to an electrode was measured using the following procedure: i) a solution containing 0.3 nM Bt-IgG* (IgG labeled with Sulfo-TAG and biotin) in an ECL Assay Buffer was introduced into the wells of streptavidin-coated 96-well NPT or PT plates; ii) the plates were incubated for 2 h with shaking to allow the Bt-IgG* to bind the surface; iii) the plates were washed four times and 150 uL of the ECL Assay Buffer was added and iv) the ECL from the label was measured. The assay buffer background was measured by introducing 150 uL of an ECL Assay Buffer into a streptavidin-coated plate and measuring the ECL. The ECL signal from free ECL labels in solution was measured by introducing a solution containing 10 nM IgG* (IgG labeled with Sulfo-TAG but not biotin) into the wells of streptavidin-coated 96-well NPT or PT plates and measuring the ECL.

Tables IIa and IIb presents the results of the experiments on NPT and PT plates, respectively. The results show that a variety of tertiary amines were suitable for use as coreactants. In general, the introduction of functionalization appeared to improve the ratio of bound to free signals. Tertiary amines having N-substituted morpholine core or, even more advantageously, a di-N-substituted piperazine core (especially, PIPES, HEPES, POPSO, HEPPSO and EPPS) appeared to be especially well suited for distinguishing bound vs. free signals (especially on NPT surfaces). There was some difference in the relative performances on PT and NPT plates, e.g., MOPS was found to perform particularly well on PT plates while bis-Tris-Propane gave exceptionally high signals on NPT plates.

ECL was also measured using coreactants in comparable buffers, except they did not include detergent or Tween 20 was used as the detergent. Two coreactants other than TPA stood out as having very low dependence on the presence or absence of Triton X-100 (N,N-bis-(hydroxyethyl)-N-4-aminobutanesulfonic acid and TPA dimer). These detergents have bound/free ratios than TPA and are especially suitable for unwashed assays having detergent sensitive components.

Additional experiments showed that these coreactants could be used in ECL Assay buffers buffered with a variety of different pH buffers, e.g., GlyGly, Gly, Tris, Tricine and phosphate.

TABLE IIa

| NPT Plates<br>Tertiary Amine | ECL<br>Background | Free | Bound | Bound<br>Background | Bound<br>Free |
|---|---|---|---|---|---|
| N-2-Hydroxypiperazine-N-2-ethanesulfonic acid (HEPES) | 171 | 3716 | 73897 | 432 | 21 |
| Piperazine-N,N'-bis-4-butanesulfonic acid | 109 | 311 | 12490 | 115 | 61 |
| Homopiperidine-N-3-propanesulfonic acid | 921 | 13833 | 11683 | 13 | 1 |
| Piperazine-N,N'-bis-3-propanesulfonic acid | 92 | 362 | 12318 | 134 | 45 |
| Piperidine-N-3-propanesulfonic acid | 861 | 9417 | 16067 | 19 | 2 |
| (3-[N-Morphilino)-3-propane sulfonic acid (MOPS) | 177 | 658 | 5857 | 33 | 12 |
| Piperazine-N-2-hydroxyethane-N'-3-methylpropanoate | 128 | 340 | 12346 | 96 | 58 |
| Piperazine-N,N'-bis-3-methylpropanoate | 76 | 210 | 5377 | 71 | 40 |
| 1,6-diaminohexane-N,N,N',N'-tetraacetic acid | 471 | 2522 | 29011 | 62 | 14 |
| N,N-bis-(hydroxyethyl)-N-4-aminobutanesulfonic acid | 1446 | 5541 | 27561 | 19 | 6 |
| N,N-bis propyl-N-4-aminobutanesulfonic acid | 564 | 13795 | 49778 | 88 | 4 |
| piperazine-N,N'-bis(2-ethane sulfonic acid) (PIPES) | 163 | 777 | 41418 | 254 | 67 |
| N-tris(hydroxymethyl)methyl-2-aminoethane sulfonic acid (TES) | 282 | 804 | 16062 | 57 | 30 |
| 1,3-Bis[tris(hydroxymethyl)methylamino]propane (bis-Tris propane) | 252 | 5207 | 61712 | 245 | 12 |
| 3-Dimethylamino-1-propanol | 236 | 2946 | 18403 | 78 | 7 |
| 1-Dimethylamino-2-propanol | 741 | 3463 | 22446 | 30 | 8 |
| N,N,N',N'-tetrapropylpropane-1,3,-diamine | 260 | 2397 | 36137 | 139 | 17 |
| MSD Assay Buffer (TPA) | 490 | 15407 | 51137 | 104 | 3 |
| Piperazine-N,N'-bis(2-hydroxypropane)sulfonic acid (POPSO) | 283 | 1995 | 86494 | 306 | 50 |
| 2-hydroxy-3-[4-(2-hydroxyethyl)piperazin-1-yl]propane-1-sulfonic acid (HEPPSO) | 225 | 1482 | 81888 | 364 | 65 |
| 3-[4-(2-hydroxyethyl)piperazin-1-yl]propane-1-sulfonic acid (EPPS) | 215 | 1545 | 79148 | 368 | 59 |
| N,N-bis(2-hydroxyethyl)-2-aminoethane sulfonic acid (BES) | 57 | 97 | 2009 | 35 | 49 |

TABLE IIb

| PT Plates Tertiary Amine | ECL Background | Free | Bound | Bound Background | Bound Free |
|---|---|---|---|---|---|
| N-2-Hydroxypiperazine-N-2-ethanesulfonic acid (HEPES) | 148 | 363 | 4233 | 29 | 19 |
| Piperazine-N,N'-bis-4-butanesulfonic acid | 111 | 152 | 750 | 7 | 16 |
| Homopiperidine-N-3-propanesulfonic acid | 447 | 4347 | 14130 | 32 | 4 |
| Piperazine-N,N'-bis-3-propanesulfonic acid | 88 | 120 | 499 | 6 | 13 |
| Piperidine-N-3-propanesulfonic acid | 376 | 2234 | 6148 | 16 | 3 |
| (3-[N-Morphilino)-3-propane sulfonic acid (MOPS) | 294 | 388 | 4221 | 14 | 42 |
| Piperazine-N-2-hydroxyethane-N'-3-methylpropanoate | 155 | 234 | 1624 | 10 | 19 |
| Piperazine-N,N'-bis-3-methylpropanoate | 182 | 287 | 1807 | 10 | 15 |
| 1,6-diaminohexane-N,N,N',N'-tetraacetic acid | 389 | 1160 | 7898 | 20 | 10 |
| N,N-bis-(hydroxyethyl)-N-4-aminobutanesulfonic acid | 297 | 452 | 5560 | 19 | 34 |
| N,N-bis propyl-N-4-aminobutanesulfonic acid | 247 | 3685 | 16465 | 67 | 5 |
| piperazine-N,N'-bis(2-ethane sulfonic acid) (PIPES) | 297 | 452 | 5560 | 19 | 34 |
| N-tris(hydroxymethyl)methyl-2-aminoethane sulfonic acid (TES) | 324 | 455 | 3050 | 9 | 21 |
| 1,3-Bis[tris(hydroxymethyl)methylamino]propane (bis-Tris propane) | 181 | 382 | 2559 | 14 | 12 |
| 3-Dimethylamino-1-propanol | 207 | 1079 | 5414 | 26 | 6 |
| 1-Dimethylamino-2-propanol | 545 | 1332 | 6903 | 13 | 8 |
| N,N,N',N'-tetrapropylpropane-1,3,-diamine | 237 | 983 | 9468 | 40 | 12 |
| MSD Assay Buffer (TPA) | 295 | 7162 | 18915 | 64 | 3 |
| Piperazine-N,N'-bis(2-hydroxypropane)sulfonic acid (POPSO) | 338 | 657 | 3842 | 11 | 11 |
| 2-hydroxy-3-[4-(2-hydroxyethyl)piperazin-1-yl]propane-1-sulfonic acid (HEPPSO) | 142 | 207 | 749 | 5 | 9 |
| 3-[4-(2-hydroxyethyl)piperazin-1-yl]propane-1-sulfonic acid (EPPS) | 132 | 207 | 803 | 6 | 9 |
| N,N-bis(2-hydroxyethyl)-2-aminoethane sulfonic acid (BES) | 112 | 118 | 636 | 6 | 87 |

7. INCORPORATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

What is claimed is:

1. A kit suitable for use in an electrochemiluminescence method comprising, one or more containers configured to receive a sample, in said one or more containers, an electrode, wherein said electrode comprises a binding domain of a binding reagent immobilized thereto, said binding domain configured to form a complex with a peptide or a protein of said sample, a pH buffer and an ECL co-reactant, wherein said pH buffer has a concentration of less than 5 mM inorganic phosphate and comprises glycylglycine or a combination of glycylglycine and tris[hydroxymethyl]aminomethane, and said ECL co-reactant comprises a tertiary amine, and wherein said electrode is configured to contact said pH buffer and said ECL co-reactant and said electrode is configured to apply electrochemical energy to said sample, ECL co-reactant and said pH buffer.

2. A kit suitable for use in an electrochemiluminescence method comprising, one or more containers configured to receive a sample, in said one or more containers, an electrode, wherein said electrode comprises a binding domain of a binding reagent immobilized thereto, said binding domain configured to form a complex with a peptide or a protein of said sample, a pH buffer, wherein said pH buffer has a concentration of less than 5 mM inorganic phosphate and comprises glycylglycine or a combination of glycylglycine and tris[hydroxymethyl]aminomethane, an Ru- or Os-containing ECL label and an ECL co-reactant, said composition being substantially free of inorganic phosphate, and wherein said electrode is configured to contact said pH buffer and said ECL co-reactant and said electrode is configured to apply electrochemical energy to said sample, ECL co-reactant and said pH buffer.

3. A kit suitable for use in an electrochemiluminescence method comprising, one or more containers configured to receive a sample, in said one or more containers, an electrode, wherein said electrode comprises a binding domain of a binding reagent immobilized thereto, said binding domain configured to form a complex with a peptide or a protein of said sample, a pH buffer and tripropylamine, wherein said pH buffer has a concentration of less than 5 mM inorganic phosphate and comprises glycylglycine or a combination of glycylglycine and tris[hydroxymethyl]aminomethane, said composition being substantially free of inorganic phosphate, and wherein said electrode is configured to contact said pH buffer and said tripropylamine and said electrode is configured to apply electrochemical energy to said sample, said pH buffer and said tripropylamine.

4. A kit suitable for use in an electrochemiluminescence method comprising, one or more containers configured to receive a sample, in said one or more containers:(a) an electrode, wherein said electrode comprises a binding domain of a binding reagent immobilized thereto, said binding domain configured to form a complex with a peptide or a protein of said sample (b) tripropylamine having a concentration ranging from 50 to 1000 mM and (c) a pH buffer having a concentration ranging from 50 to 1000 mM, said pH buffer has a concentration of less than 5 mM inorganic phosphate and comprises glycylglycine or a combination of glycylglycine and tris[hydroxymethyl]aminomethane, and wherein said electrode is configured to contact said pH buffer and said tripropylamine and said electrode is configured to apply electrochemical energy to said sample, said pH buffer and said tripropylamine.

5. The kit of claim 3, comprising tripropylamine in a concentration ranging from 50 to 1000 mM.

6. The kit of claim 1, wherein said kit is free of inorganic phosphate.

7. The kit of claim 1, further comprising one or more components selected from the group consisting of kinases and kinase substrate.

8. The kit of claim 1, further comprising one or more components selected from the group consisting of phosphatase and phosphatase substrate.

9. The kit of claim 1, wherein said pH buffer is glycylglycine.

10. The kit of claim 1, wherein said pH buffer is tris[hydroxymethyl]aminomethane.

11. The kit of claim 2, wherein said ECL co-reactant comprises a tertiary amine.

12. The kit of claim 2, wherein said ECL co-reactant comprises tripropylamine (TPA).

13. The kit of claim 1, further comprising ethylenedyaminetetraacetic acid (EDTA).

14. The kit of claim 1, wherein said pH buffer is glycylglycine and said composition further comprises ethylenedyaminetetraacetic acid (EDTA).

15. The kit of claim 1, further comprising KOH.

16. The kit of claim 1, further comprising an ECL moiety.

17. The kit of claim 1, further comprising an ECL moiety which is capable of repeatedly emitting electrochemiluminescence.

18. The kit of claim 1, further comprising a metal containing ECL moiety.

19. The kit of claim 1, further comprising a Ru- or Os-containing ECL label.

20. The kit of claim 1, further comprising one or more substances selected from the group consisting of a salt, a detergent, a preservative, a chelator and an anti-foaming agent.

21. The kit of claim 1, further comprising a surfactant.

22. The kit of claim 1, wherein said kit is aqueous.

23. The kit of claim 1, wherein said kit further comprises at least one separate component in which one or more members of the group consisting of an ECL moiety (i) and electrolyte (ii) is included.

24. A method of effecting a specific-binding assay, either qualitatively or quantitatively, in a composition comprising: (a) a pH buffer having a concentration of less than 5 mM inorganic phosphate and comprises glycylglycine or a combination of glycylglycine and tris[hydroxymethyl]aminomethane (b) a phosphor-specific antibody and (c) an ECL label.

25. The method of claim 24, wherein said composition further comprises an ECL co-reactant.

26. The method of claim 24, wherein said composition further comprises a phospho-specific antibody.

27. A method of effecting a specific-binding non-wash assay, either qualitatively or quantitatively, in a well having one or more assay domains with binding reagents immobilized thereon using a composition comprising a pH buffer and an ECL label, wherein said pH buffer has a concentration of less than 5 mM inorganic phosphate and comprises glycylglycine or a combination of glycylglycine and tris[hydroxymethyl]aminomethane.

* * * * *